US009839486B2

(12) United States Patent
Hughes et al.

(10) Patent No.: US 9,839,486 B2
(45) Date of Patent: Dec. 12, 2017

(54) SYSTEMS AND METHODS FOR PATIENT-BASED COMPUTER ASSISTED SURGICAL PROCEDURES

(75) Inventors: Michael Dean Hughes, Cordova, TN (US); Jeffrey A. Sharp, Salt Lake City, UT (US)

(73) Assignee: Smith & Nephew, Inc., Memphis, TN (US)

( * ) Notice: Subject to any disclaimer, the term of this patent is extended or adjusted under 35 U.S.C. 154(b) by 1434 days.

(21) Appl. No.: 13/087,284

(22) Filed: Apr. 14, 2011

(65) Prior Publication Data
US 2011/0257653 A1    Oct. 20, 2011

Related U.S. Application Data

(60) Provisional application No. 61/324,207, filed on Apr. 14, 2010, provisional application No. 61/324,692, filed on Apr. 15, 2010.

(51) Int. Cl.
| *A61B 17/17* | (2006.01) |
|---|---|
| *A61B 34/20* | (2016.01) |
| *A61F 2/38* | (2006.01) |
| *A61B 90/00* | (2016.01) |
| *A61B 34/10* | (2016.01) |
| *A61B 34/30* | (2016.01) |

(52) U.S. Cl.
CPC ............ *A61B 34/20* (2016.02); *A61B 34/10* (2016.02); *A61B 17/1764* (2013.01); *A61B 34/30* (2016.02); *A61B 2034/102* (2016.02); *A61B 2034/105* (2016.02); *A61B 2034/108* (2016.02); *A61B 2034/207* (2016.02); *A61B 2034/2051* (2016.02); *A61B 2034/2055* (2016.02); *A61B 2034/2063* (2016.02); *A61B 2034/2072* (2016.02); *A61B 2090/3983* (2016.02); *A61F 2/3859* (2013.01)

(58) Field of Classification Search
USPC .............................. 606/79, 86 R, 99; 700/98
See application file for complete search history.

(56) References Cited

U.S. PATENT DOCUMENTS

| 5,290,281 A | * | 3/1994 | Tschakaloff ..................... 606/28 |
|---|---|---|---|
| 5,564,437 A | * | 10/1996 | Bainville et al. ............. 600/587 |
| 6,827,723 B2 | | 12/2004 | Carson |
| 6,923,817 B2 | | 8/2005 | Carson et al. |

(Continued)

OTHER PUBLICATIONS

International Search Report and Written Opinion dated Dec. 23, 2011 for PCT/US2011/032573.

(Continued)

*Primary Examiner* — David Bates
(74) *Attorney, Agent, or Firm* — David Chambers

(57) ABSTRACT

Surgical systems and methods are disclosed for creating a 3D model of a patient's affected area using an imaging device, using the model to determine an implant orientation and position, creating patient-matched instrumentation, placing the patient-matched instrumentation on the patient's anatomy, registering a computer-assisted surgical tool, and acquiring registration information. The methods and systems also include associating the surgical tool with a computer to perform a computer assisted surgery. Also disclosed are embodiments of patient-matched instrumentation to acquire registration information.

16 Claims, 41 Drawing Sheets

(56) References Cited

U.S. PATENT DOCUMENTS

| | | |
|---|---|---|
| 6,928,742 B2 | 8/2005 | Broers et al. |
| 7,237,556 B2 | 7/2007 | Smothers et al. |
| 7,477,926 B2 | 1/2009 | McCombs |
| 7,547,307 B2 | 6/2009 | Carson et al. |
| 7,611,520 B2 | 11/2009 | Broers et al. |
| 7,662,156 B2 | 2/2010 | Carson |
| 7,764,985 B2 | 7/2010 | McCombs et al. |
| 7,862,570 B2 | 1/2011 | Russell et al. |
| 8,221,430 B2 * | 7/2012 | Park et al. ............ 606/88 |
| 2006/0161052 A1 | 7/2006 | Colombet et al. |
| 2007/0288030 A1 * | 12/2007 | Metzger et al. ......... 606/87 |
| 2008/0306490 A1 | 12/2008 | Lakin et al. |
| 2008/0319448 A1 | 12/2008 | Lavallee et al. |
| 2010/0030231 A1 | 2/2010 | Revie et al. |

OTHER PUBLICATIONS

Australian Patent Office, Patent Examination Report No. 1, dated Oct. 19, 2015, 4 pages.

* cited by examiner

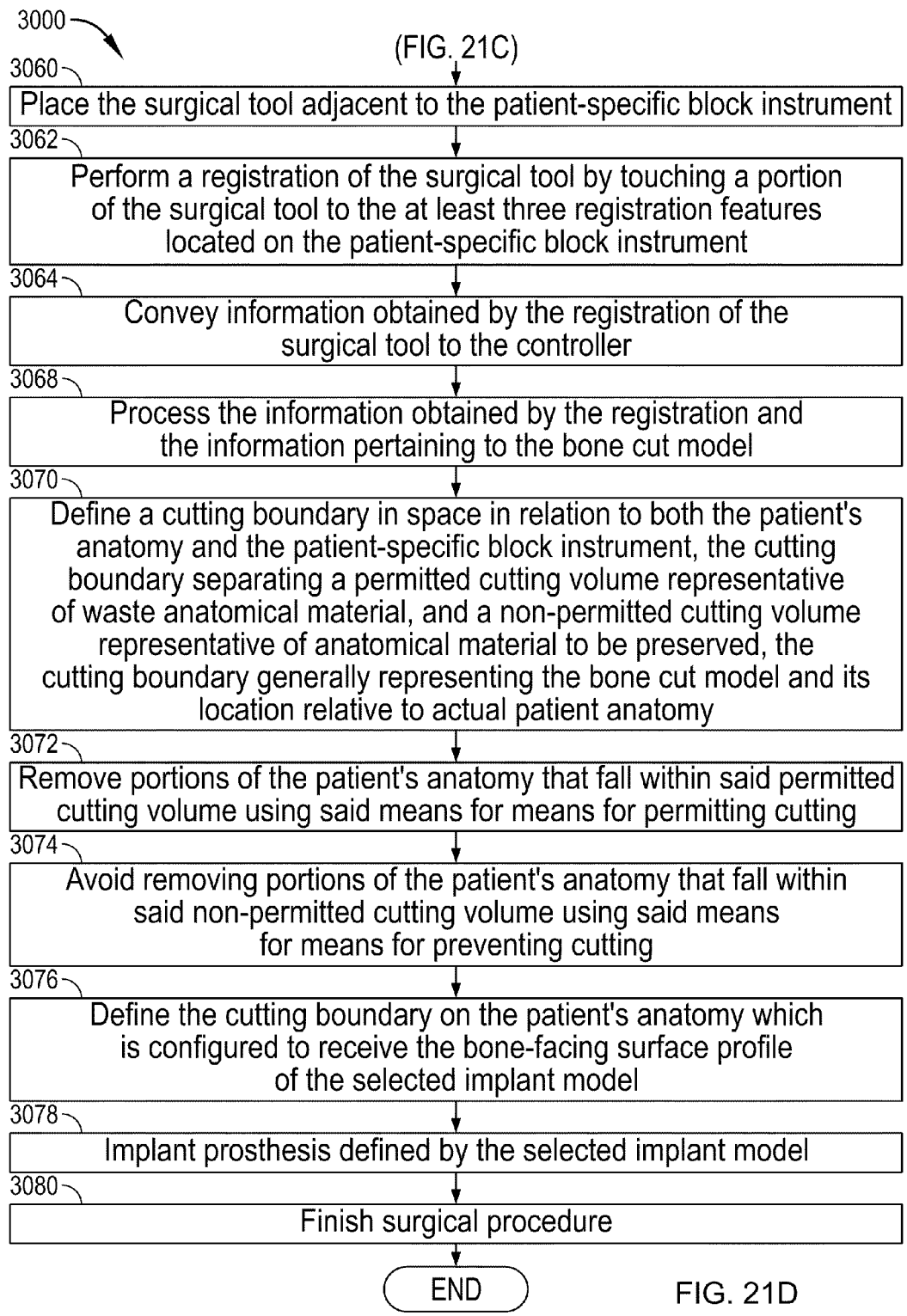

SYSTEMS AND METHODS FOR PATIENT-BASED COMPUTER ASSISTED SURGICAL PROCEDURES

CROSS-REFERENCE TO RELATED APPLICATIONS

This application claims the benefit of priority of U.S. provisional application Ser. No. 61/324,207 filed Apr. 14, 2010, and U.S. provisional application Ser. No. 61/324,692 filed Apr. 15, 2010. The disclosures of each of the foregoing applications are hereby incorporated by reference in their entirety.

BACKGROUND

Orthopedic implants are used for resurfacing or replacing joints, such as knees, hips, shoulders, ankles, and elbows that typically experience high levels of stress and wear or traumatic injury. Implants used to replace these joints must be strong and able to withstand the daily stress and wear at these joints, especially for weight-bearing knee and hip replacements. But providing a sufficiently strong implant that also fits properly is challenging. Traditional orthopedic implants are made from polymer, ceramic, metal or other appropriate material and formed so that they fit the patient's bone securely. In knee replacement surgeries, for example, typical approaches involve cutting the end of the tibia and/or femur, then fitting a new implant to the cut end. The size of the implant is typically determined by the surgeon based on hand measurements and visual estimates. The size and fit between the bone and implant can vary—in some cases being too loose, and in others too tight.

Computer assisted methods have been developed that provide a graphical image of the resected bone and design software that allow the surgeon to install the implant to fit the surgical site more precisely. During a computer-assisted surgery (CAS), a surgeon registers the patient's anatomical site by touching various landmarks around the patient's joint using a registration tool. Once the registration process is completed, the surgeon uses a surgical tool (e.g., cutter) to resect the bone in the patient's joint. The surgical tool may be guided by a computer assisted system.

There are, however, drawbacks to conventional registration processes. A surgeon typically uses a foot pedal or needs an assistant's help during the registration process. The surgeon is required to hold the registration tool steady against a smooth bone surface. While the surgeon is holding the tool, the surgeon's assistant notifies the computer what registration point the surgeon is registering. Also, to register a single point the surgeon may need to change the orientation of the registration tool in various angles with respect to the registration point to ensure that a tracking camera accurately captures the location. This registration process is tedious, time-consuming, and prone to errors.

Conventional CAS systems also include a reference array, which is made of light-reflective material that can be viewed on video camera and used to track the position of a surgical tool during the surgery. The reference array is positioned on the patient or near the patient, but it can be bumped easily and misaligned if anyone moves the operating table or pushes the reference array. When that happens, the patient's anatomic location needs to be re-registered, which prolongs the surgery time. Unfortunately, the surgeon may find it difficult to re-locate the same anatomical landmark sites registered previously, and therefore it may be difficult to re-register the site, possibly reducing the accuracy of the surgical procedure.

In some cases, a surgeon defines a bone cutting boundary pre-operatively based on the 3D model of a patient's joint or MRI or CT image of the patient. Therefore, the accuracy of the surgical procedure may depend on how well the registered bone (which is based on 3D model or an image of the patient) matches the physical bone. That matching can be difficult to achieve. There is a need for a registration process that allows the surgeon to repeatedly and more efficiently register a patient's bone for surgery.

SUMMARY

Disclosed herein are surgical systems and methods that provide a 3D model of a patient's affected area using imaging devices. The systems and methods (and various related apparatuses) use the model to determine an optimal implant and/or optimal implant position through virtual implantation and biomechanical simulation techniques. The techniques, in some implementations, create patient-matched instrumentation that conforms in one spatial orientation to the patient's anatomy, placing the patient-matched instrumentation on the patient's anatomy, registering a surgical tool with the patient-matched instrumentation while the patient-matched instrumentation remains in contact with the patient's anatomy, acquiring information about a relative position and/or orientation of the surgical tool, and associating the surgical tool with a computer. The computer preferably uses a controller, tracking hardware, tracking software, and a file containing information about one or more pre-planned anatomical modifications. The controller serves to instruct the surgical tool to perform or not perform one or more surgical functions according to the position of the surgical tool relative to the patient during surgery. Information about the surgical procedure to be performed is stored in the computer and is used in conjunction with the registration information obtained by the patient-matched instrumentation to control the one or more surgical functions of the tool.

Also disclosed are embodiments of patient-matched instrumentation which may be used to acquire registration information.

Certain embodiments include a patient-matched surgical guide for registering a location of a patient's bone, for example a tibia. By registering the location of the bone, the surgeon can more easily make appropriate cuts within the bone to prepare it for implant placement or other surgery. The surgical guide includes an inner surface that conforms to the patient's bone and a body having a registration site that receives a registration tool of a medical device for communicating the location of that registration tool to a processor. The registration site includes one or more registration points that correspond to one or more reference markers shown or described in an image of the patient's bone, for example, a computer image. The registration sites are easy to spot on the surgical guide. So, if the surgeon needs to re-register the device during surgery, he or she can easily find the reference markers on the registration site, rather than having to remember the location of the registration marker on the bone itself The image of the patient's bone is used to create a three-dimensional model of the patient's bone, and the registration points chosen so as to correspond to related reference markers of the three-dimensional model of the patient's bone. The markers preferably define a spatial relationship with respect to the articulating surfaces of the patient's bone. For example, a point may be created in the body of a polymer guide at a location that is chosen to overlay a pre-selected site on the resected femur, when the guide is interfitted to the resected femur end. The surgeon selects the reference marker site in the graphical computer image of the bone then generates the guide body with a point that corresponds to that site.

The patient-matched guide has a surface that interfits with the anatomical location which will be cut during the surgery. The surface may be structured so that it interfits with the guide in a single spatial orientation, for ease of alignment. The surface may be partially spherical.

The guide is also preferably prepared from a graphical image of the patient's bone, which is taken by creating a graphical image of the surgery site, and then using that image to create a three-dimensional model. In certain embodiments, the image is of a virtual surgery model, and a physical model is created from that virtual model by rapid prototyping.

Certain embodiments include a system for registering a location of a patient's anatomic portion using a guide that is structured as a patient-matched block. The block has an anatomy-facing surface that conforms to a patient's bone and a connector. A mount attaches to the bone and the connector and is configured to receive an array to communicate a location of the bone to a computer assisted surgical system. The mount may be positioned in a fixed spatial relationship with respect to the anatomy-facing surface. The mount may be included on a cutting tool that interfaces with the registration site.

In certain embodiments, a system is provided for performing a computer-assisted surgical procedure for implanting a prosthetic device to a patient. The system includes a patient-matched block having a registration site and an inner surface that is configured to conform to a patient's bone. The system includes a surgical tool with a cutting tip that interfaces with the registration site to identify a location of the registration site, and a processor that tracks the location of the tool with respect to the location of the patient's bone. In certain implementations, the cutting tip includes a center that corresponds to the registration point of the patient-matched block.

Systems disclosed herein may use a computer having tracking hardware, tracking software, and a controller for guiding the surgical tool according to a file containing a surgical plan. The systems may include one or more files that include data that identifies the location of one or more registration sites on the guide (e.g., the patient-matched block) relative to the patient's bone. In certain implementations, a tracking receiver is provided for communication with the processor, the tracking receiver being configured to identify the location of the registration site by identifying the location of an array attached to a registration tool. The tracking receiver may be structures as an array. The tracking receiver may be mounted to a housing. The housing may be located on the cutting tool. The array may be included as part of a housing that mounts the patient-matched block to the patient.

Methods of use and methods of operation are also contemplated. Certain embodiments include a method of performing a computer-assisted surgical procedure for implanting a prosthetic device to a patient. Such method includes the steps of creating a three-dimensional model of a portion of the patient's bone, determining an optimal implant or implant position, and creating a body (e.g., a patient-matched block) that conforms to a portion of the bone, the body having a registration site that corresponds to a predetermined location on the bone. In certain implementations, methods include placing a patient-matched block on the patient's body, registering a surgical tool by touching a portion of the surgical tool to the registration site, defining a cutting boundary in relation to the patient's anatomy, and removing a portion of the patient's anatomy by making cuts within the cutting boundary.

In certain methods, a virtual implantation file is created. The file includes processor instructions for establishing a cutting boundary and representing that boundary electronically. The cutting boundary may be displayed on a monitor. If a cutting tool crosses the boundary, the imaging devices detect the crossing and signal to the processor to warn the surgeon.

In certain implementations, methods are provided operating a surgical alignment guide. Such methods include providing a patient-matched block, the block having at least one registration site and an inner surface that conforms to an anatomic portion of the patient. Such methods may further provide a surgical tool with an alignment point or tip that interfaces with the registration site. The methods may also involve positioning the alignment point with respect to the at least one registration site to align the guide and the tool.

Tracking tools may be used. In certain implementations, the methods involve tracking the position of a surgical tool relative to a reference array to identify the position of the tool. In certain implementations, a processor defines a cutting boundary having one or more pre-planned optimized resections of the patient's anatomy. The location of the surgical tool is tracked relative to the cutting boundary.

In certain implementations, the surgeon removes a portion of the patient's bone positioned within the cutting boundary by tracking the position of the surgical tool with respect to the patient's bone and cutting the bone along a path defined by a processor.

In certain embodiments, a method is provided for implanting a prosthetic device in a patient. The methods include applying a patient-matched surgical apparatus about a portion of a patient's bone, the apparatus having an inner surface that conforms to the bone portion and an alignment site that receives a registration tool. In certain implementations, the methods include joining the alignment site with a registration tool and tracking a location of a surgical tool with respect to the patient's bone by detecting the position of the surgical tool with respect to an array.

In various implementations, a registration tool is used. The registration tool may be formed with or include a distal tip of a surgical tool. In certain implementations, the registration tool is a distal tip of a surgical tool. In certain implementations, two or more arrays are used to help electronically define the cutting boundary. A first array is mounted to the patient or at some site in the surgery room nearby, and the surgical tool includes a second array.

In certain implementations, a registration tool includes a connector that interfaces with the alignment site. The registration tool may interfit directly with an array or indirectly via an adaptor for receiving the array.

Certain systems may also be used or provided, having a patient-matched surgical apparatus with an inner surface that conforms to the patient's bone and an alignment site, a registration tool configured to interface with the alignment site to identify the location of the patient's bone, and a processor that tracks a location of a surgical tool with respect to an array.

Further features, aspects, and advantages of various embodiments are described in detail below with reference to the accompanying drawings.

BRIEF DESCRIPTION OF THE DRAWINGS

The accompanying drawings, which are incorporated in and form a part of the specification, illustrate embodiments and together with the description, serve to explain various examples of the disclosed methods and systems. In the drawings:

FIGS. 21a-d schematically illustrate a method of using a surgical system according to some embodiments;

DETAILED DESCRIPTION OF EXAMPLE EMBODIMENTS

The figures illustrate certain implementations of systems and methods used to perform a computer assisted surgical procedures using a patient-matched alignment guide. The patient-matched alignment guide helps a surgeon more accurately register a patient's bone during a computer-assisted surgical procedure. The patient-based alignment guide also helps to speed up the registration process compared to a manual registration process. In certain implementations, the patient-matched alignment guide includes an inner surface that conforms to the patient's bone and a body having a registration site that receives a registration tool of a medical device for communicating the location of that registration tool to a processor.

Figure 1:
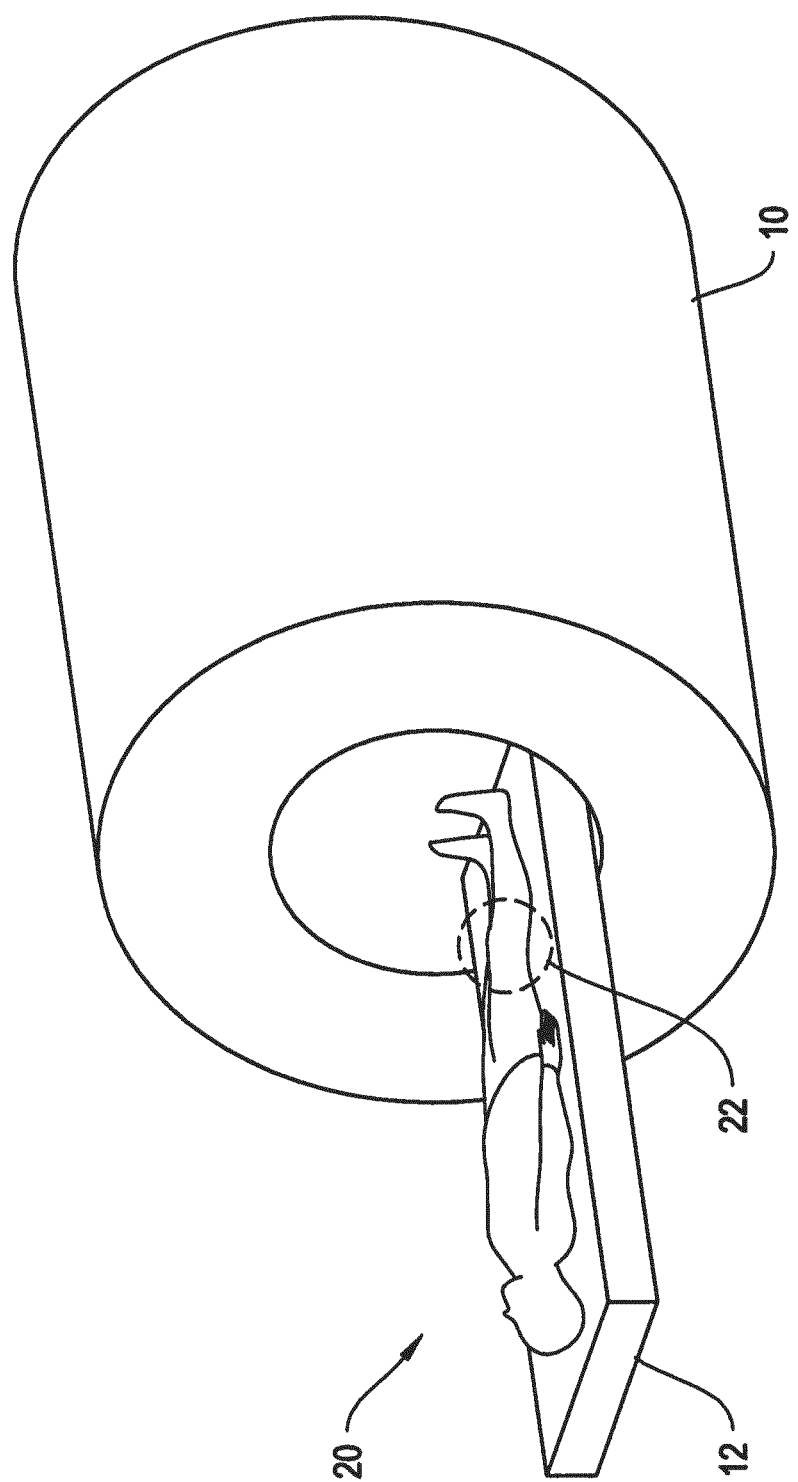
FIG. 1 shows a step of scanning a patient to obtain patient image data.

Referring to the accompanying drawings in which like reference numbers indicate like elements, FIG. 1 illustrates a step of scanning a patient 20 to obtain patient information. Devices for obtaining patient information may include, for instance, X-ray, computerized tomography (CT), magnetic resonance imaging (MRI), ultrasound, or other similar imaging devices. A patient 20 is subjected to scanning 10 and may be held still by a platform 12 or one or more jigs or fixtures (not shown) to reduce imaging artifacts. Image data of an affected area 22 of the patient is collected. While the particular embodiments shown and described herein generally relate to knee joints, it should be understood that the methods disclosed may be advantageously used in conjunction with any surgical procedure. For instance, the systems and methods described herein may be equally applicable to arthroplasty or reconstruction of the hip, foot, arm, elbow, shoulder, neck, spine, cranio-maxiofacial (CMF) regions, and extremities, without limitation.

Figure 2:
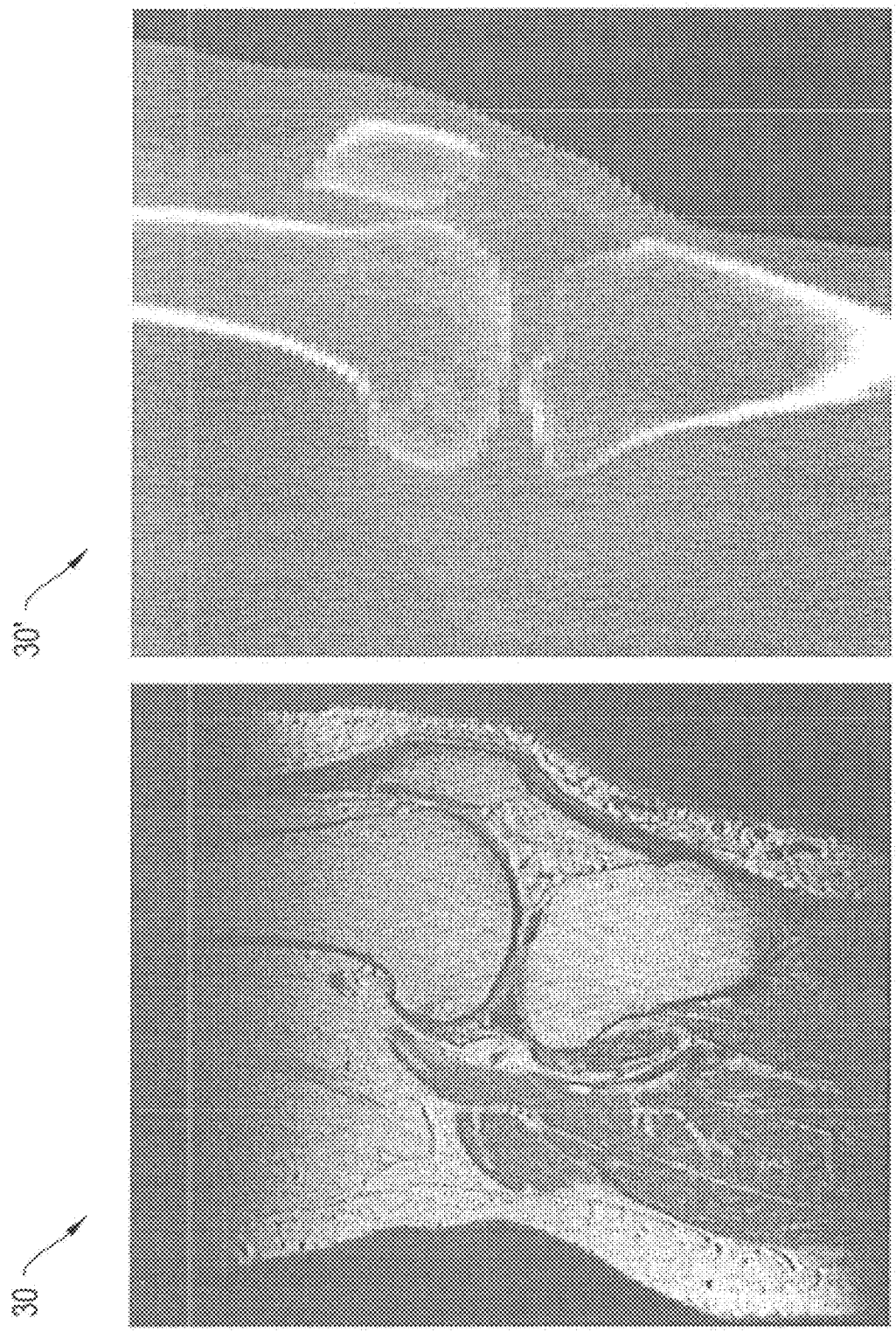
FIG. 2a shows MRI patient image data according to some embodiments.
FIG. 2b shows CT patient image data according to other embodiments.

FIGS. 2A and 2B show patient data according to two exemplary embodiments. FIG. 2A shows an MRI scan image slice 30, and FIG. 2B shows a CT scan image slice 30'.

Figure 3:
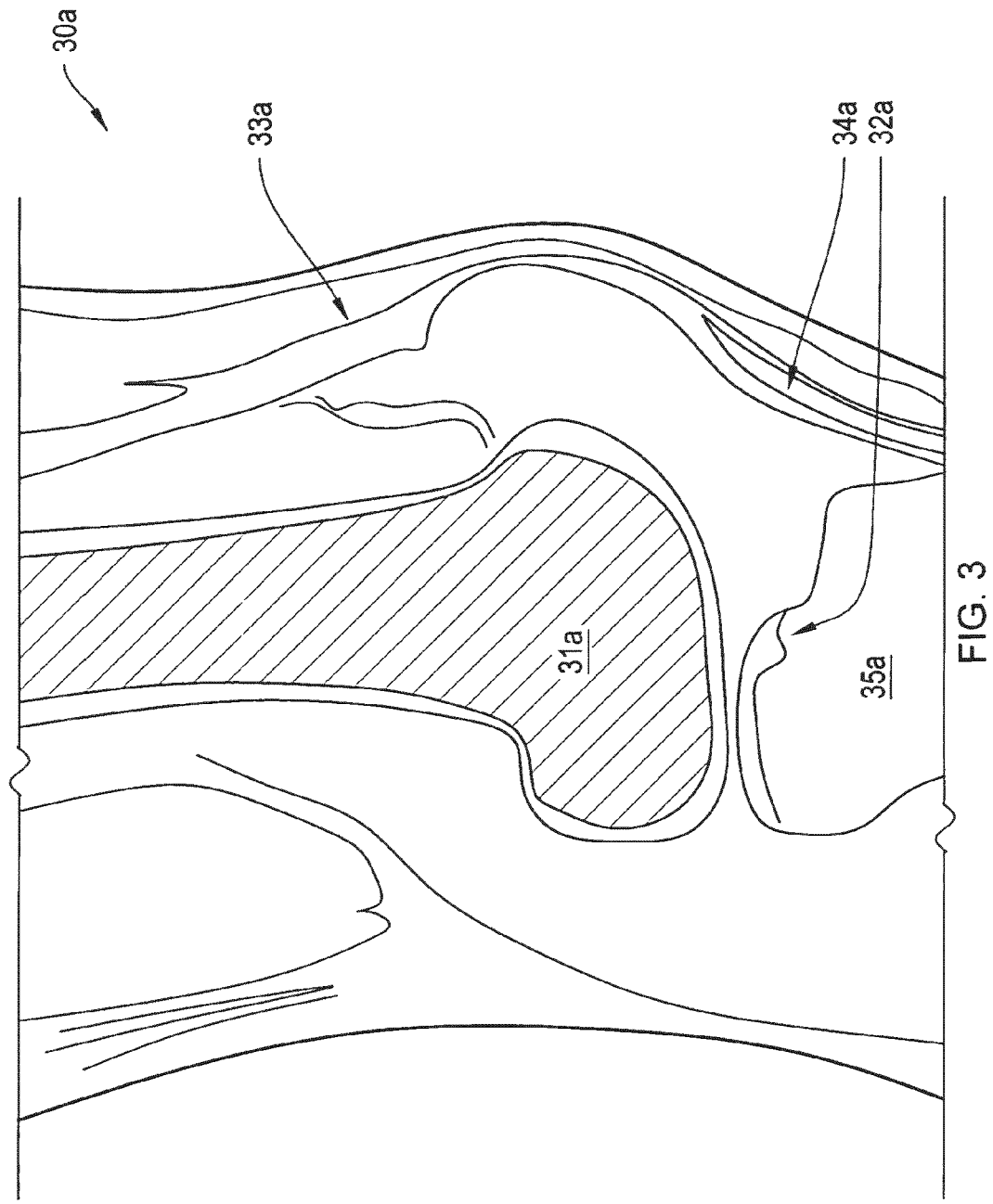
FIG. 3 shows a step of segmenting patient data.

FIG. 3 shows a step within a segmentation process. One 30a of a plurality of image slices is imported into a computer having segmentation software such as MIMICS. MIMICS is a registered trademark of Materialise Inc. headquartered at Technologielaan 15, 3001 Leuven, Belgium. Regions of bone, cartilage, and soft tissues are separated in the image slice 30a, as well as in the remaining plurality of image slices. In the particular embodiment shown, a knee image 30a slice is segmented to separate femoral bone and cartilage 31a from tibial bone and cartilage 35a and soft tissues such as cruciate ligaments 32a, quadriceps tendon 33a, and patellar ligament 34a. Segmentation may be automatic, manual, or a combination thereof.

Figure 4:
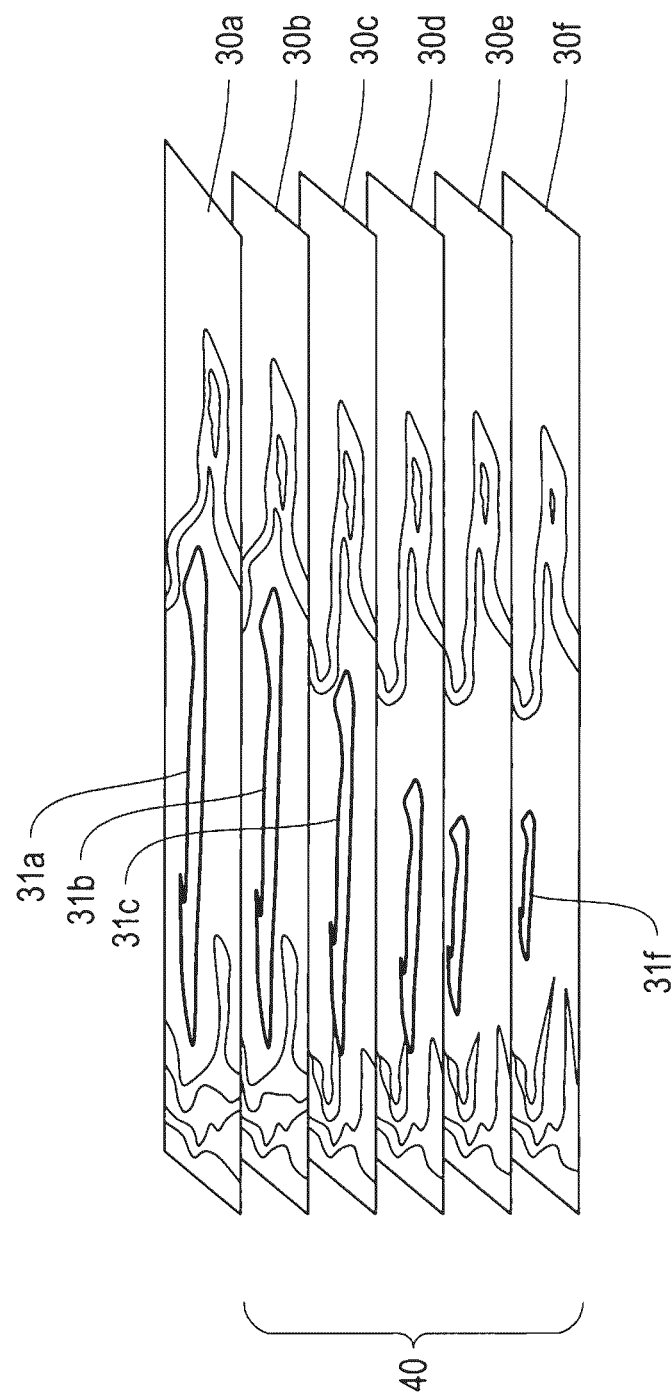
FIG. 4 shows a step of assembling segmented patient data.
Figure 5:
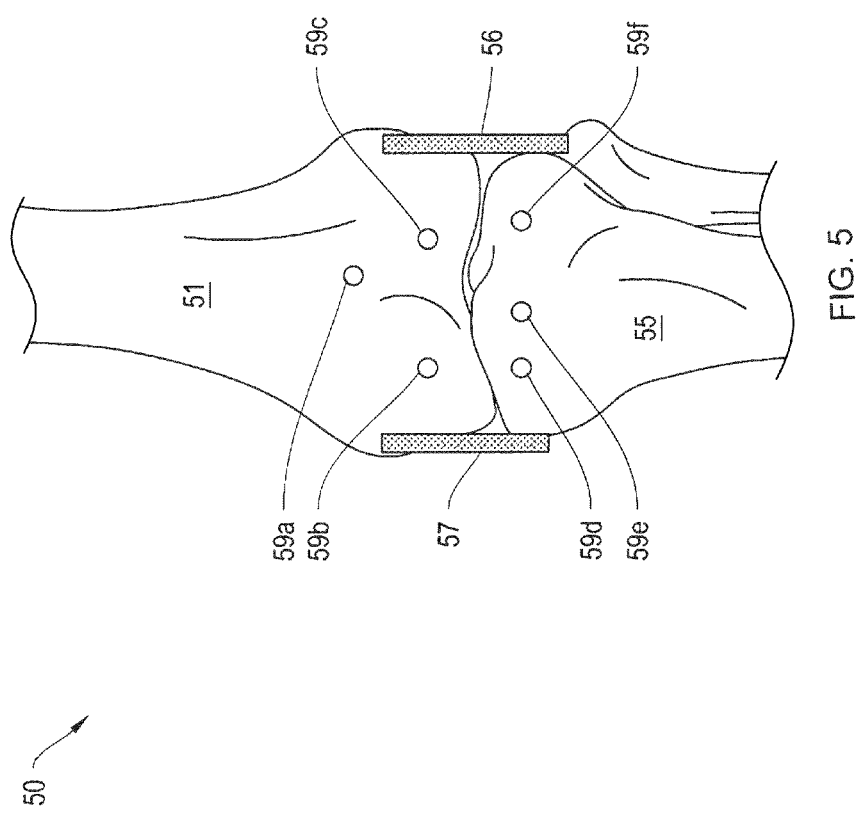
FIG. 5 shows a step of creating a patient model using segmented patient data.

FIG. 4 shows a plurality 40 of segmented image slices 30a-f each having segmented portions 31a-f. The plurality of segmented image slices 30a-f are imported into modeling software to create a 3D model 50 of the patient's affected anatomy as shown in FIG. 5. The 3D model 50 may serve as a working model for use in biomechanical simulations as will be discussed hereinafter. The 3D model 50 may incorporate bone, cartilage, and/or soft tissues derived from the patient scan. In the particular embodiment shown, the 3D model 50 is a model of patient's affected knee joint and includes a bone, cartilage, and cruciate ligament model comprising characteristics of an individual patient's femur 51, tibia 55, fibula, lateral collateral ligament 56, and medial collateral ligament 57. In this case, anterior and posterior cruciate ligaments are omitted from the 3D model 50 because a bicruciate-stabilized implant is used. A series of reference point markers 59a-f may be incorporated into the model, each marker 59a-f defining spatial relationships between the markers and anatomic landmarks or features present in the 3D model 50. The locations of these markers 59a-f are selected to correspond with certain anatomic landmarks or articulating surfaces of the femur 51 and tibia 55. More particularly, the markers 59a-59c may be selected to correspond to the anatomic surfaces of the medial and lateral condyles of femur and medial and lateral epicondyles of the femur. One of the reference point markers 59*a*-59*c* may correspond to the distal condylar line of the femur, the Whiteside line, or the mechanical axis of the leg. Additional reference point markers 59*c*-59*f* that correspond to the tibial anatomical landmarks such as medial and lateral condyles of tibia and tibial tuberosity may be selected. Other reference points could be used, for example one or more of the anatomic axis, mechanical axis, A-P depth, M-L width, joint line, ACL attachment, tibial sulcus, medial malleolus, posterior condylar axis, and distal femoral condyle.

Figure 6:
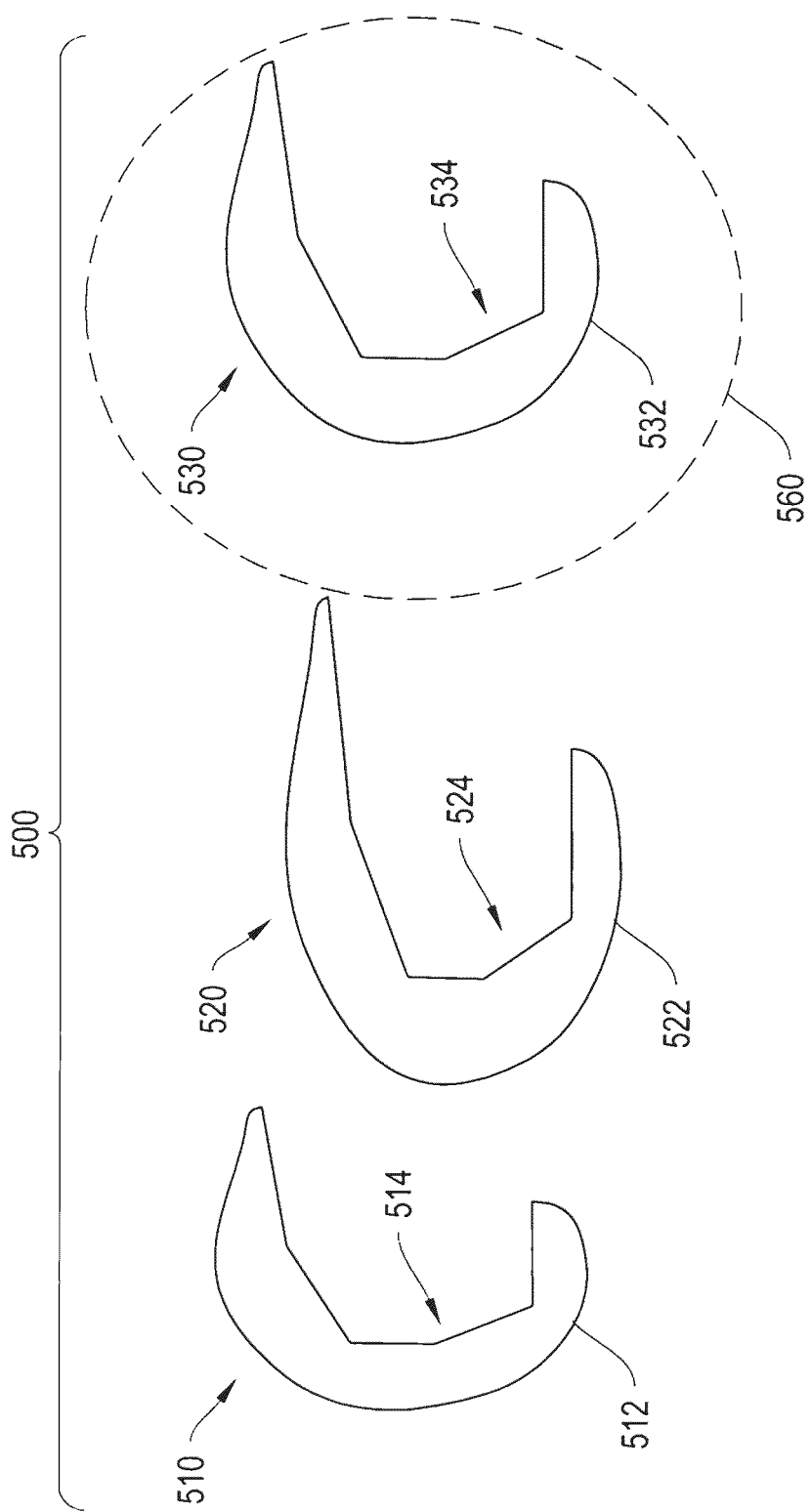
FIG. 6 shows a step of creating or selecting an implant from a database of implants, based on the patient model.

FIG. 6 illustrates the step of selecting 560 an implant 530, such as a femoral component of a knee prosthesis from a series 500 of implants 510, 520, 530 according to some embodiments. The prosthesis components may comprise articulating surfaces 512, 522, 532 having different geometries and/or bone-facing surface portions 514, 524, 534 having different geometries. The selection 560 may be provisionally determined by computer software, by an engineer, by a health care provider, sales associate, or technician based on parameters of the 3D model 50. In certain implementations, the implant 530 is created based on the patient model 50. The bone-facing surface portions 514, 524, 534 may be shaped specifically to conform to follow the patient's unique joint shape and localized contours along the surface of the joint. In certain implementations, the implant 530 is selected from a library that is pre-loaded with implants with varying shape and size.

Figure 7:
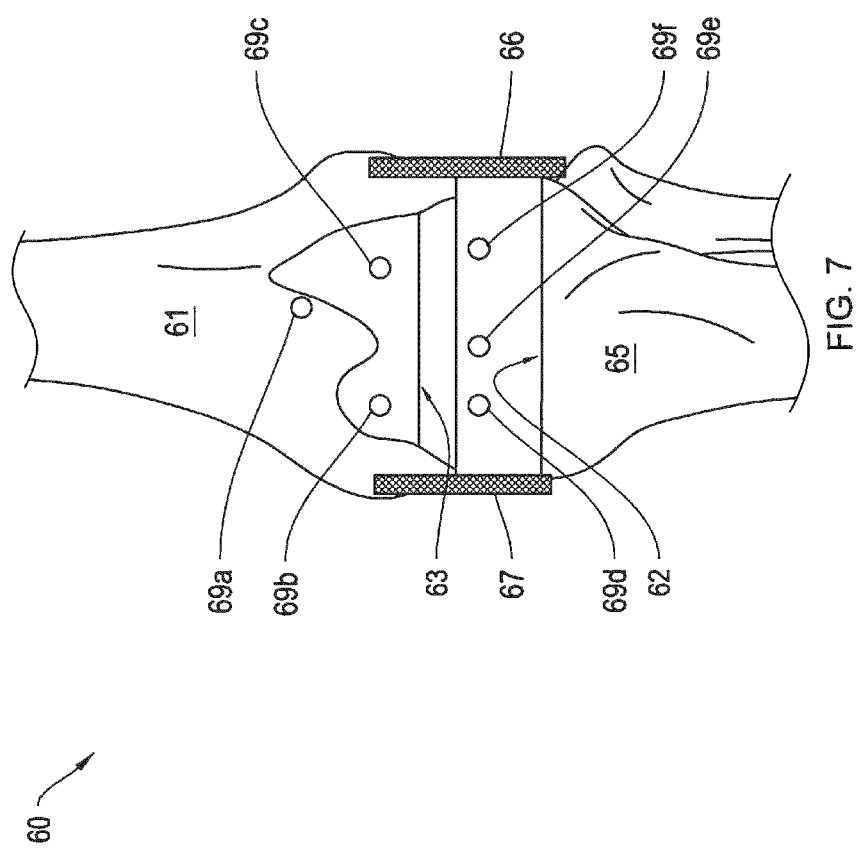
FIG. 7 shows a step of performing a virtual surgical step on the patient model to create an incomplete virtual surgery model.
Figure 23:
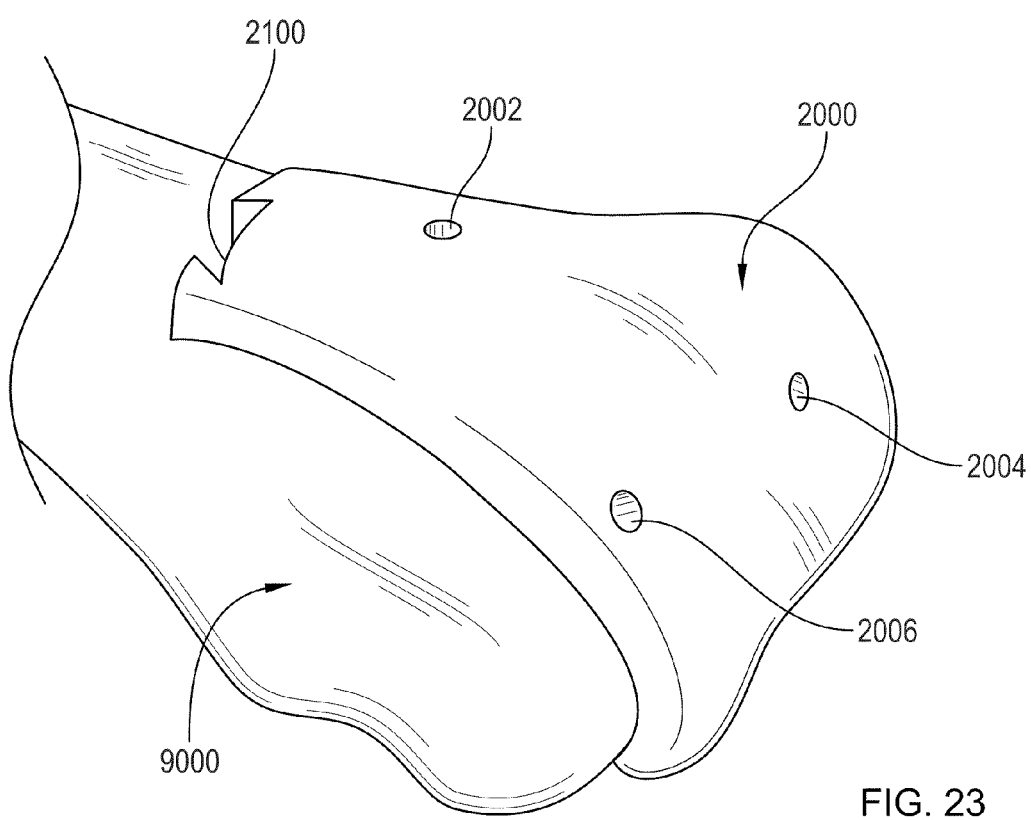

As shown in FIG. 7, the 3d patient model 50 may be converted to an incomplete virtual surgery model 60 comprising one or more surgical modifications to the 3D patient model 50, based on the implant selection 560 and the attributes 532, 534 of the selected implant 530. The incomplete virtual surgery model 60 may comprise, for instance, one or more virtual resections or cuts 63, 62 to a femur 61 and tibia 65, respectively. In certain embodiments, one or more reference point markers 69*a-f* are maintained in the same spatial locations relative to the anatomic portions 61, 65, 66, 67 of the model 60 as the markers 59*a-f* in the 3D patient model 50. For instance, markers 69*a-f* may define additional spatial relationships between the markers 69*a-f* and provisionally determined virtual resections or cuts 62, 63 of the tibia 65 and femur 61. In certain embodiments, the point markers 69*a-f* are picked after the virtual resections or cuts are determined in respect to the computer model. In certain embodiments, one or more reference point markers 69*a-f* may be selected so as to define a cutting a plane. In certain embodiments, one or more of the reference point makers 69*a-f* corresponds to one or more locations of a pin hole disposed on a patient-matched instrument (e.g., cutting block). In certain implementations, the patient-matched instrument may include a slot for receiving a cutting blade for making a distal resection and two pin holes for preventing the rotation of the instrument once fitted to the patient's bone. In alternative implementations, one or more additional or alternative reference markers could be used to designate locations in the bone or bone model for making one or more holes or cuts within the patient's bone to help assist with registration of a cutting device if the patient-matched device is removed during surgery. One or more such markers could be identified in the model 50 or virtual surgery model 60 to correspond to one or more pin holes, slots or other cuts to be made in the patient's bone to assist in the registration and guiding of the surgical tool. For example, one or more alternative markers could be included in a model to denote a place for inserting one or more holes in the patient matched device (e.g., a patient-matched block 200) and correspondingly in the patient's bone overlaid by the patient matched device. For example one or more holes such as 2004 or 2006 of FIG. 23 et seq. (discussed below) could be placed within the patient-matched block, and corresponding holes drilled or cut into the patient's bone in locations directly beneath the block under such holes. After inserting such holes, if the block is removed prior to the resection, the health care provider could use the holes or slots in the bone as reference points for re-registration of the tool or guiding the tool to make cuts during the resection.

Figure 8:
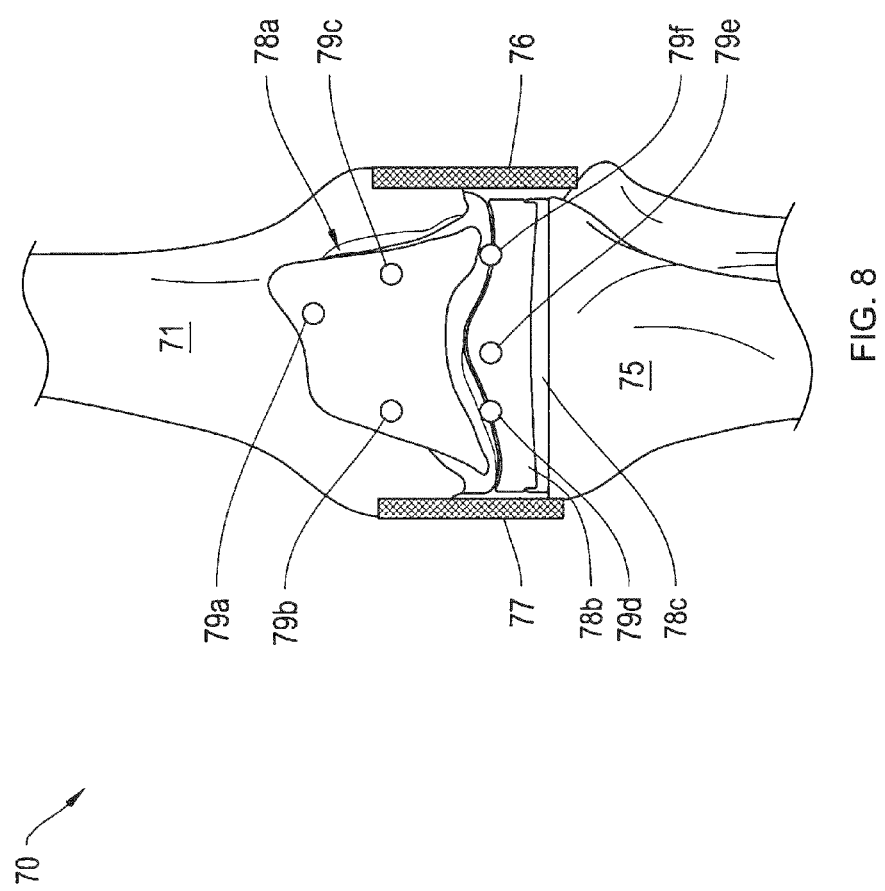
FIG. 8 shows a step of performing one or more other surgical steps on the patient model to create a completed virtual surgery model.

As shown in FIG. 8, the virtual surgery model 60 may be converted to a completed virtual surgery model 70 comprising one or more surgical modifications 63, 62 to the 3D patient and incomplete virtual surgery models 50, 60 based on the implant selection 560 and the attributes 532, 534 of the selected implant 530. The completed virtual surgery model 70 may comprise, for instance, one or more implant components such as a femoral component 78*a*, a tibial articular insert component 78*b*, and a tibial baseplate component 78*c*. One or more reference point markers 79*a-f* are maintained in the same spatial locations relative to the anatomic portions 71, 75, 76, 77 of the completed virtual surgery model 70 as the markers 59*a-f*, 69*a-f* in the 3D patient and incomplete virtual surgery models 50, 60. For instance, markers 79*a-f* may define additional spatial relationships between the markers 79*a-f* and a provisionally determined virtual articular surfaces and bone facing interface surfaces of the implant components 78*a-c*.

Figure 9:
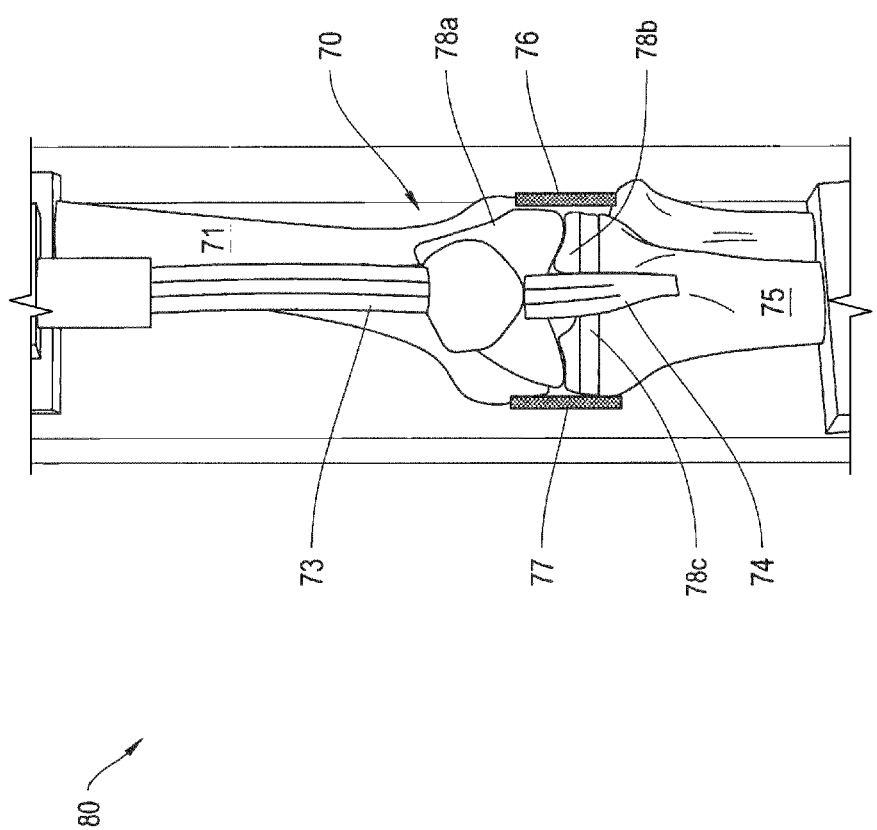
FIG. 9 shows a step of loading a completed virtual surgery model into a biomechanical simulator and running iterative simulations.

As shown in FIG. 9, the completed virtual surgery model 70 may be imported into biomechanical simulation software such as KNEESIM by LIFEMOD to determine one or more predicted performance characteristics of the implant components 78*a-c*. "LifeMOD" and "KneeSIM" are trademarks of LifeModeler, Inc., 2730 Camino Capistrano, Suite 7, San Clemente, Calif. The simulation model 80 may be iteratively run with different completed virtual surgery models 70—each completed virtual surgery model 70 incorporating different implant selections 560. Selections 560 may have different implant attributes including differences in size, articular geometry 512, 522, and bone facing attachment geometries 514, 524. Alternatively, the simulation model 80 may be iteratively run with different completed virtual surgery models 70, each incorporating different implant positioning. For instance, in each completed virtual surgery model 70, one or more implant components 78*a-c* may be spatially oriented differently relative to the patient's anatomy 71, 75, 76, 78. Biomechanical simulation model 80 may further comprise soft tissues representative of the patient's own anatomy, such as the quadriceps muscle and tendon 73, patellar tendon 74, and collateral ligaments 76, 77.

Figure 10:
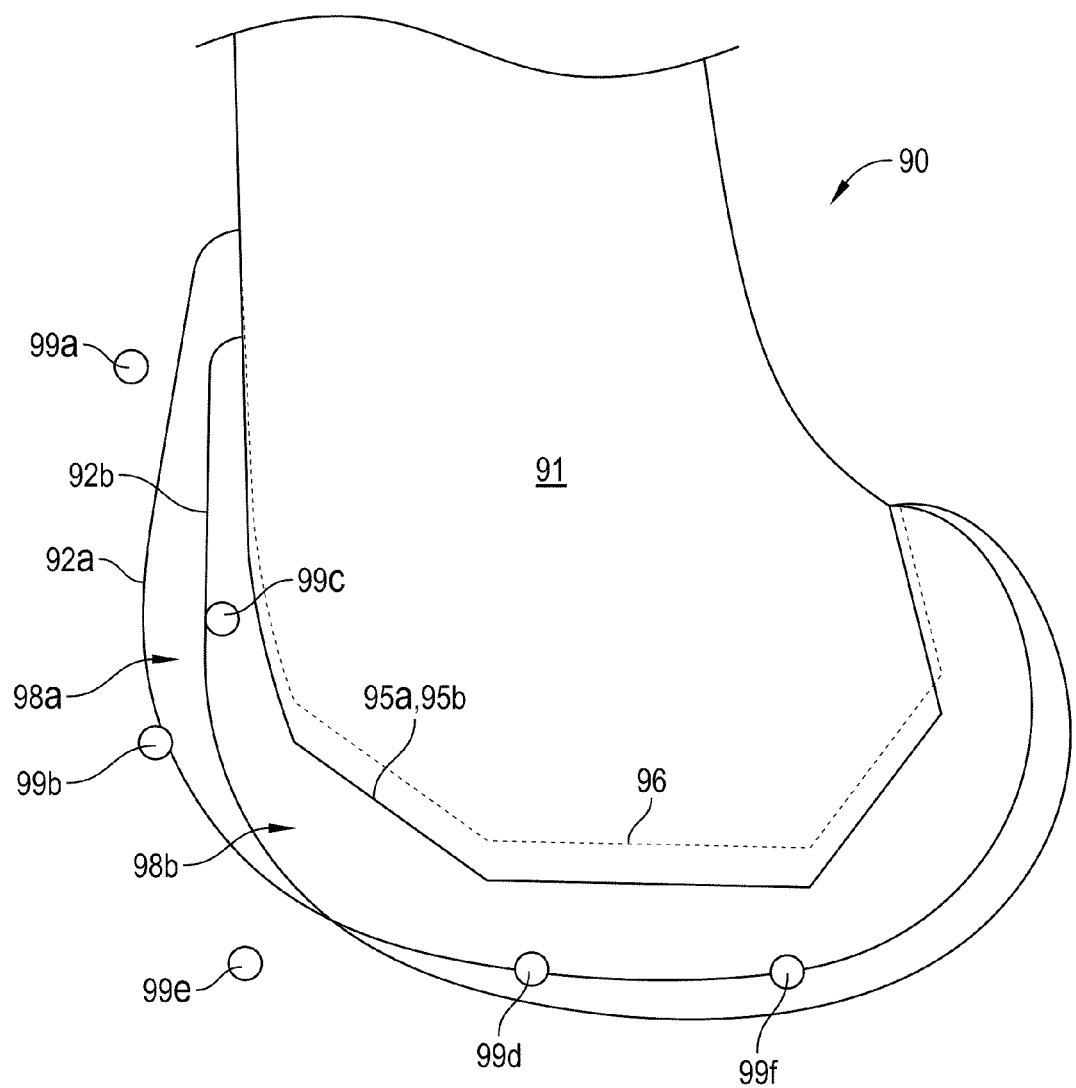
FIG. 10 shows a step of evaluating performance characteristics to determine the best implant and/or best positioning of an implant by iteratively performing the steps shown in FIGS. 6-9.

The iterative and autonomous nature of the biomechanical simulation software is advantageous because it facilitates an optimization of any one or more of: implant selection 560, implant orientation relative to the patient's anatomy, and surgical steps (e.g., positioning one or more bone cuts 62, 63). This is illustrated in FIG. 10. An iterative model 90 may be created by importing a set of parameters into one or more of the models 50, 60, 70, 80. Parameters may include, for instance, information relating to a series of implants 98*a*, 98*b* having similar bone-facing surface geometries (95*a*, 95*b*), one or more different bone-facing surface geometries (95*a*, 96), or one or more different articular surfaces (92*a*, 92*b*). As with other models 50, 60, 70, 80, the iterative model 90 may also incorporate one or more reference point markers 99*a-f* which are maintained in the same spatial locations relative to the anatomic portions 91 of the iterative model 90 as the markers 59a-f, 69a-f, 79a-f in the other models 50, 60, 70. For instance, markers 99a-f may define additional spatial relationships between the markers 99a-f and anatomy 91 or between the markers 99a-f and one or more iterative model 90 attributes 92a, 98a, 95a; 92b, 98b, 95b; 96. Biomechanical simulation, along with the preparation of the model 70 and formation of the physical model (e.g., block 200) could be performed before surgery.

Figure 11:
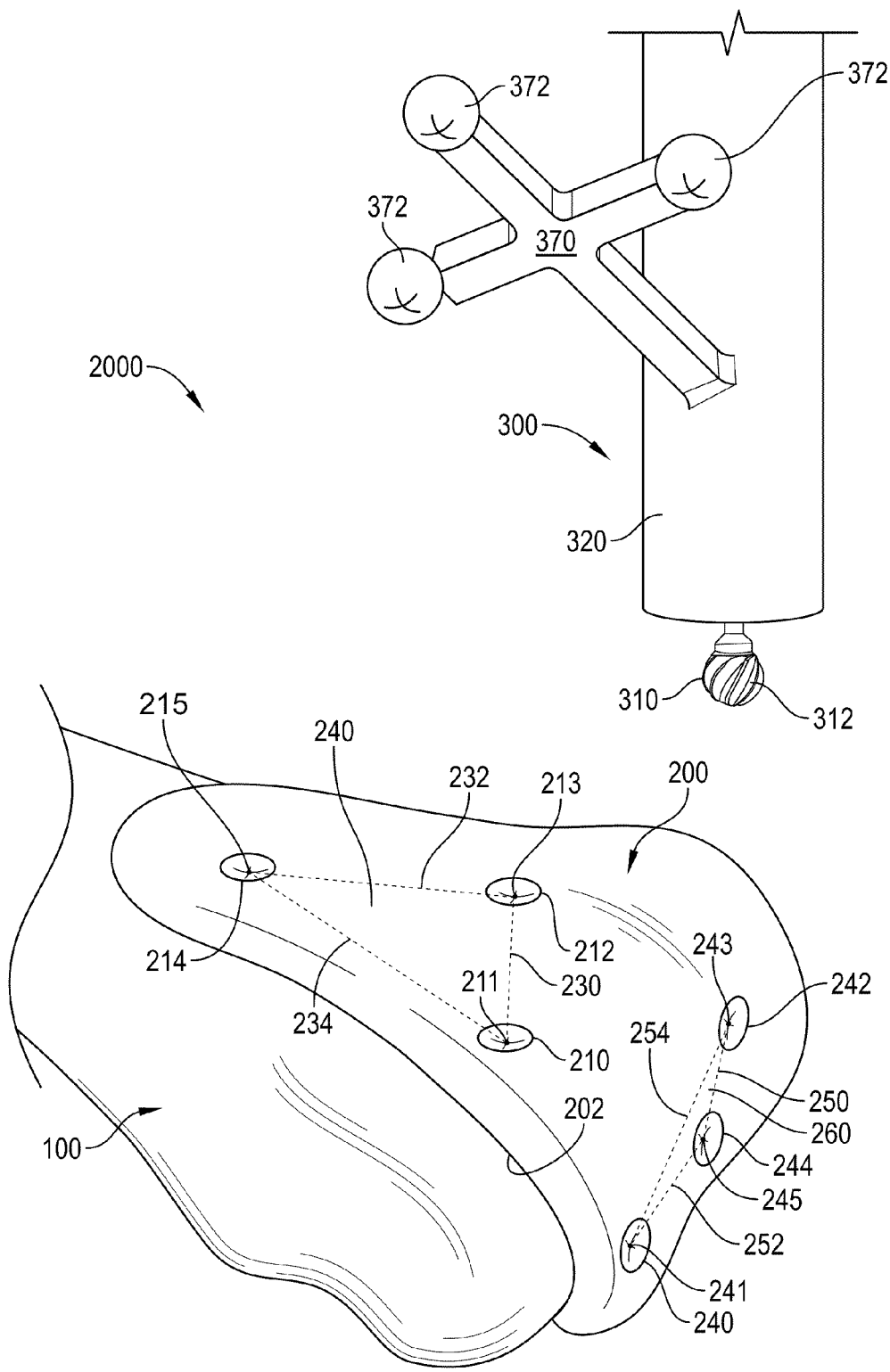
FIGS. 11-12 show portions of a surgical system according to some embodiments.

FIG. 11 shows a surgical system 2000 according to some embodiments. A patient-matched instrumentation block 200 is created using information obtained from one or more of the models 50, 60, 70, 80, 90 referenced above. The block 200 incorporates a body having a plurality of registration portions 210, 212, 214, 240, 242, 244, and a surface 202 including at least three points of contact which conforms to an anatomic portion of an affected area 22 of the scanned patient 20, for instance, the patient's distal femur 100. The surface 202 may be manufactured from the 3D model 50 (FIG. 5) of the patient. The block 200 fits to the anatomic portion of the affected area 22 in only one spatial orientation. More specifically, the surface 202 is structured specifically to match the patient's bone surface such that when the surgeon places the block 200 on the patient's joint, the patient's bone surfaces interface with the surface 202 to temporarily fix the block 200 in place with respect to the patient's bone, but because of the shape and contouring of the block, which corresponds to the bone, the block fits on the bone in only one orientation. Once fitted, the block 200 does not move or rotate with respect to the patient's bone until the surgeon physically removes the block 200 from the patient's bone. This allows the surgeon to take off the block 200 and re-fit the block 200 exactly the same way if he or she needs to re-mount the block 200 to re-register the patient's bone surface.

In the embodiment shown, the registration portions 210, 212, 214, 240, 242, 244 have generally partially spherical surfaces having center registration points 211, 213, 215, 241, 243, 245 which correspond to the one or more reference markers 59a-f, 69a-f, 79a-f, 99a-f in models 50, 60, 70, 80, 90 (described above). The block 200 is created by taking one or more of the models 50, 60, 70, 80, 90 and determining the locations of the registration portions 210, 212, 214, 240, 242, 244 that correspond to one or more reference markers 59a-f, 69a-f, 79a-f, 99a-f found in the selected model. This allows the block 200 to function as a physical surgical template that aligns virtual anatomy with the actual anatomy of the patient. In some instances, the registration points 211, 213, 215, 241, 243, 245 of each registration portion may define one or more reference planes, such as an anterior coronal plane 240 or a distal transverse plane 260. For example, femoral patient-matched instrumentation blocks 200 configured for use with the knee joint may comprise center registration points define other anatomical landmarks such as a mechanical axis 232 of the joint, an anatomic axis 234 of the joint, Whiteside's line 250, the epicondylar axis (252), or the like.

A surgical tool 300 comprising a body 320, tracking member 370, and a rotatable, reciprocating, or vibratory cutting member 310 is provided. The cutting member 310 is adapted for communication with the block 200 at a plurality of locations (i.e., at each registration portion). The tracking member 370 may be provided, for example, as an array having one or more three fiducial marker members 372 which can be tracked in space by a receiver 1010 as will be described later. Alternatively, while not shown tool 300 may comprise a receiver 1010 mounted thereto, in lieu of an array, which senses other arrays in the surgical field.

In the particular embodiment shown, the cutting member 310 has a center 312 that corresponds identically to center registration points 211, 213, 215, 241, 243, 245 of the registration portions 210, 212, 214, 240, 242, 244. A registration step may include placing the cutting member 310 into each registration portion 210, 212, 214, 240, 242, 244 of the block 200 in order to communicate spatial positioning information about the tool 300 and cutter 310 relative to both the block 200 and the patient's anatomy 100 to a computer 1020 having a controller. It should be understood that while the cutter 310 and registration portions 210, 212, 214, 240, 242, 244 are shown to comprise spherical surface portions, other shapes (e.g., conical, cylindrical), could be used, so long as the cutter 310, 312 is configured to properly register with registration points 211, 213, 215, 241, 243, 245 associated with the block 200.

Figure 12:
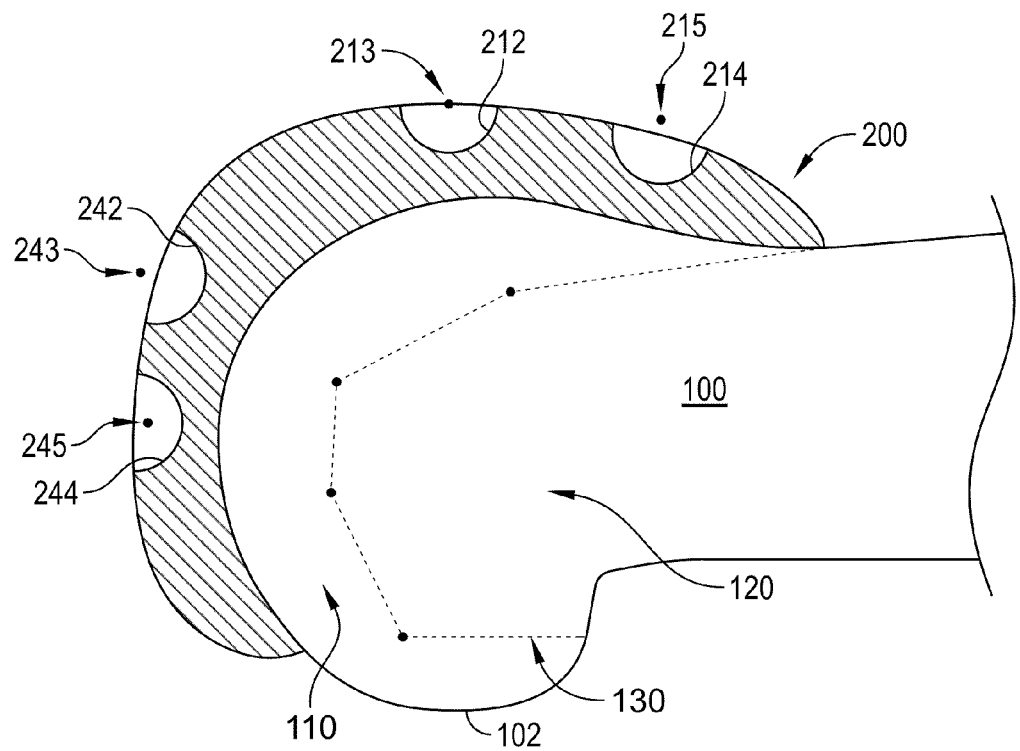

FIG. 12 shows a transverse cross-sectional view of block 200 and the relative relationships between registration portions 210, 212, 214, 240, 242, 244, registration points 211, 213, 215, 241, 243, 245, anatomy 100, 102, and one or more pre-planned optimized resections 130. Because the registration points 211, 213, 215, 241, 243, 245 are derived from and correspond to the reference markers 59a-f, 69a-f, 79a-f, 99a-f of models 50, 60, 70, 80, 90, one or more optimized surgical steps can be transferred from the virtual models 50, 60, 70, 80, 90 to the patient's actual anatomy, using the block 200 as a surgical template for aligning virtual anatomy with actual anatomy. For instance, the spatial relationships between an optimized virtual resection 63 relative to marker 69c (determined from the virtual surgery model 60 and validated for best performance using simulation models 80, 90) may directly equate to the spatial relationships between a planned actual resection 130 relative to registration points 245 on the block 200.

Figure 13:
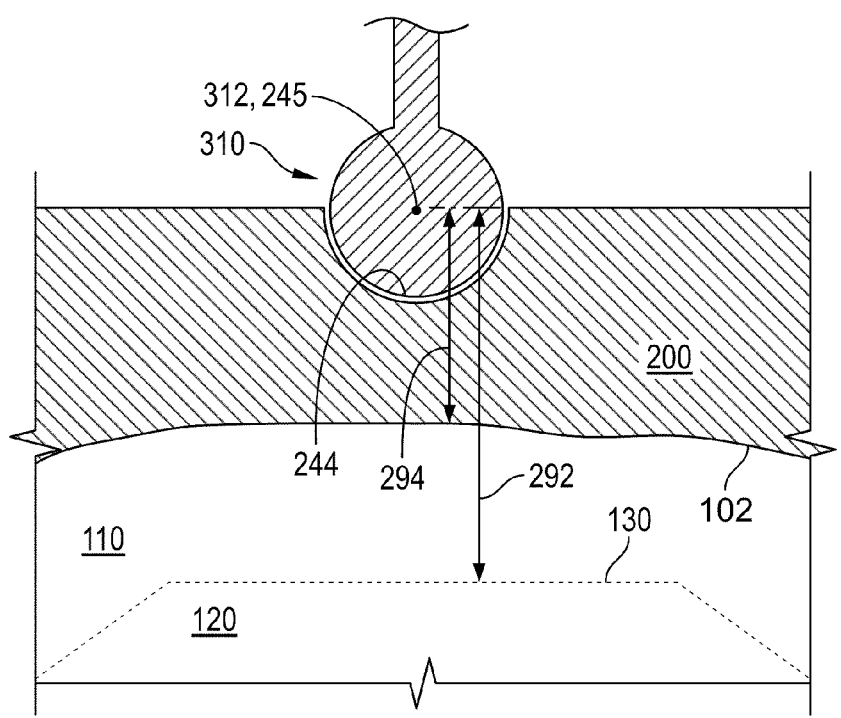
FIGS. 13-14 show a step of registering position information of a surgical system component according to some embodiments.
Figure 14:
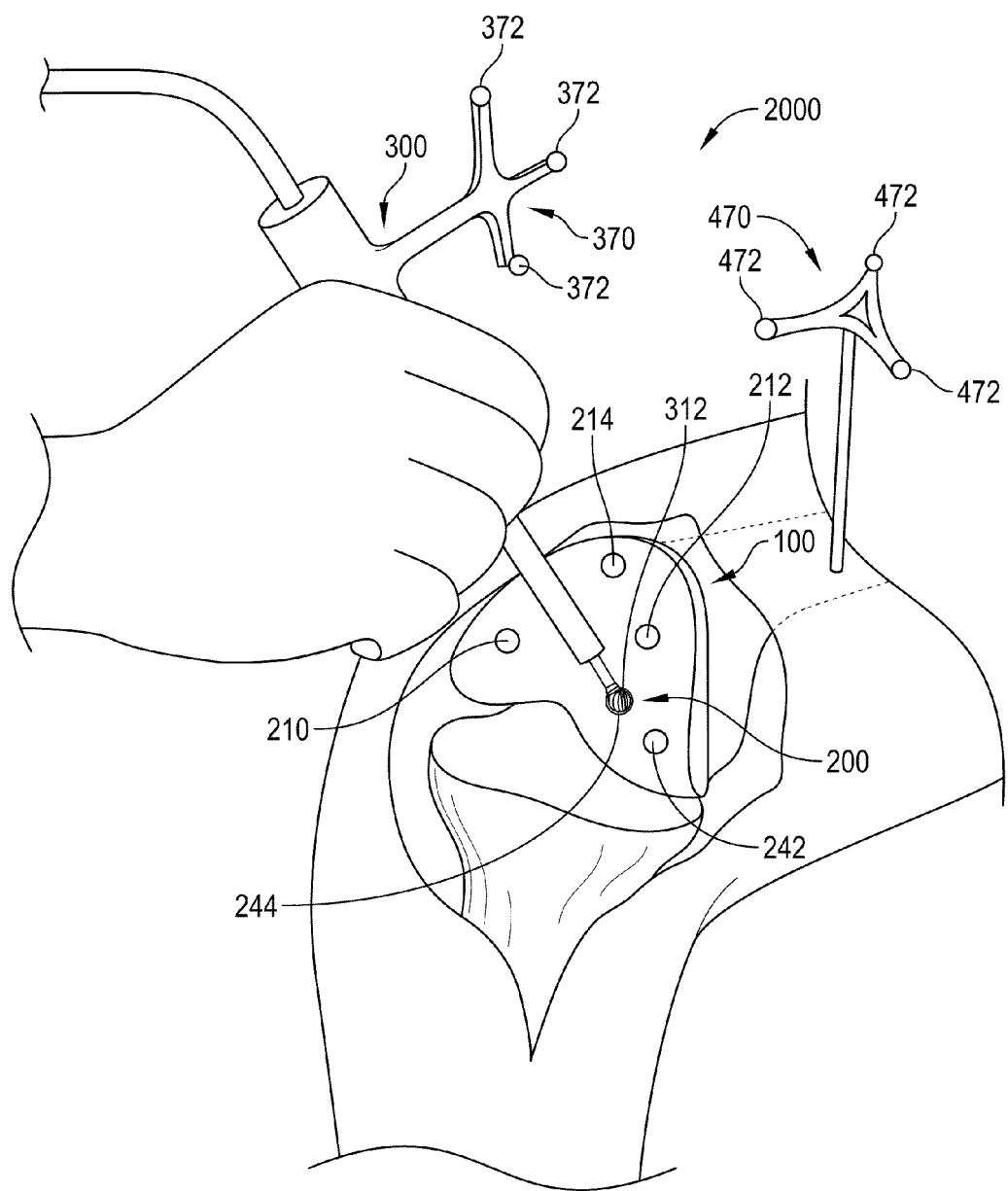

FIGS. 13 and 14 show one of a plurality of registration steps using the block 200. The cutter 310 is placed into one 244 of the plurality of registration portions, such that the cutter center 312 is aligned with the registration point 245 of the registration portion 244. The tool 300 holding the cutter 310 may be rotated around at various angles keeping the cutter 310 within the registration portion 244 to ensure a proper registration. It should be known that a separate smooth spherical ball registration tip identical in size and shape to the cutter 310 can be used in lieu of cutter 310, in order to accomplish the same registration function and reduce the possibility of teeth on the cutter 310 cutting into or damaging the block 200. During registration steps, information pertaining to relative spatial relationships 294, 292 between the cutter 310 and anatomical portions such as an articular surface 102 or one or more pre-planned optimized resections 130 located below uncut bone 110 may be transferred to a computer 1020 having a controller, or to a stand-alone computer and controlling device located on or inside the tool 300. The surgeon may input information into the computer 1020 regarding which registration point 245 or registration portion 244 is being registered at any given time. It should be noted that the one or more pre-planned optimized resections 130, while shown as a series of planar cuts, may comprise a series of curves, splines, irregularly-shaped surfaces, B-splines, and 3D surfaces to match or better suit a particular patient's anatomy. For instance, non-planar resections may be used with custom implants having matching non-planar attachment surfaces, in order reduce the total amount of bone or cartilage removal necessary to accommodate a standard implant having planar resections. The one or more pre-planned optimized resections 130 may be focused around areas of deteriorated anatomy only, resulting in more minimally-invasive surgeries and better bone conservation.

FIG. 14 illustrates the step of registering a surgical tool 300 and associated cutter 310 using a patient-matched block. After placing the block 200 on the patient's bone, one or more arrays 470 having one or more fiducial markers 472 may be secured to the patient's anatomy (e.g., the femur). The one or more arrays 470 are preferably provided adjacent to the patient's affected site (e.g., the distal femur). The surgeon places the cutter 310 of the tool 300 into one 244 of a plurality of registration portions 210, 212, 214, 242 and notifies the computer 1020 which registration portion is communicating with the cutter 310 at any given time. This may be done through a graphical user interface (GUI) or a keypad located on or communicating with the tool 300. The center of the cutter 310 is then registered with one or more of the other registration portions 210, 212, 214, 242 until the desired virtual surgery model 60 is aligned with the patient's actual anatomy 22. Since the center 312 of the cutter 310 essentially matches the spatial location of each registration point 211, 213, 215, 243, 245 on the block 200, data regarding the spatial location 294 of each registration point 245 relative to the patient's anatomy 102 are stored into the computer 1020 in a first file. A second file containing a preoperative plan, information regarding one or more surgical procedure steps, and/or a 3D image file of the one or more pre-planned optimized resections 130 is also uploaded to the computer 1020. The second file is representative of the virtual surgery model 60 and includes one or more reference markers 69a-f which are synonymous with each spatial locations 292 of each registration point 245 (the data being available at the time of manufacturing the block 200). Essentially, in the most basic sense, the second file serves as a virtual surgical blueprint for the patient-specific procedure and the first file serves as a calibration mechanism so that the surgical tool 300 can physically be used to implement the virtual surgical blueprint.

Figure 15:
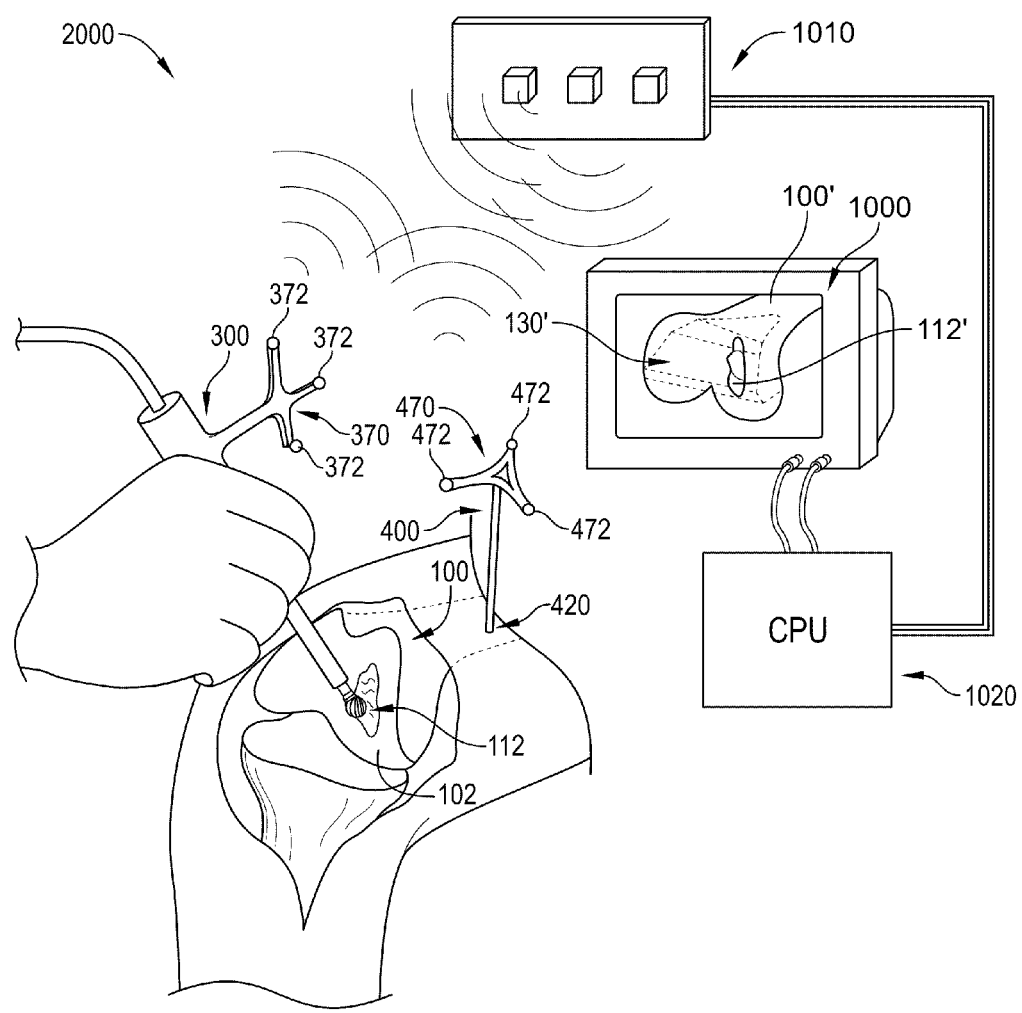
FIG. 15 shows a step of modifying anatomy based on obtained registration information and one or more pre-planned resections according to some embodiments.
Figure 16:
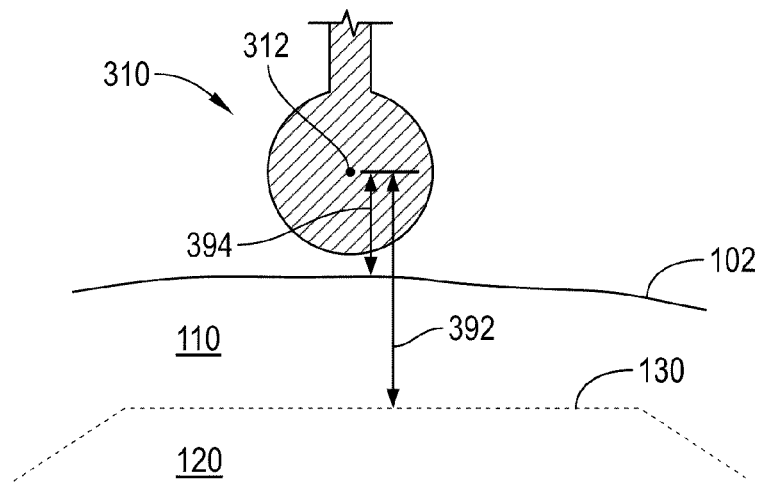
FIGS. 16-19 show surgical cutting steps using a surgical tool having a controlled functionality.
Figure 17:
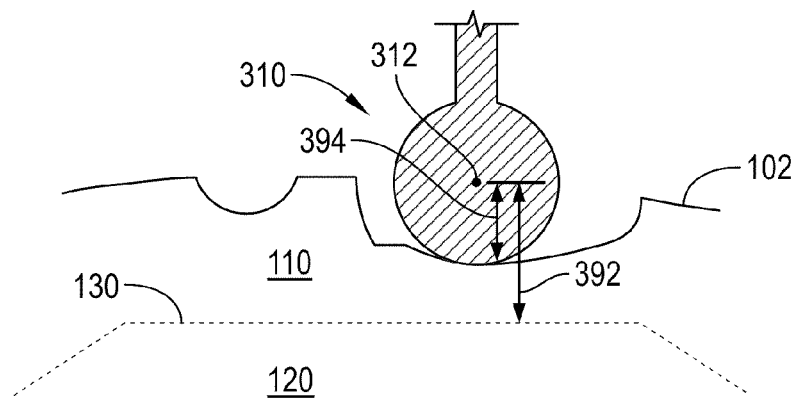

By relating the information obtained in the first file to the computer 1020, the computer's processor can determine the actual physical position and orientation of the tool 300 and cutter 310 in 3D space relative to both the patient's actual anatomy and virtual surgery model 60. The relative position and orientation of the tool 300 and cutter 310 in 3D space relative to the one or more pre-planned optimized resections 130 may also be determined using information contained within the second file and displayed on the GUI device as shown in FIG. 15.

Figure 18:
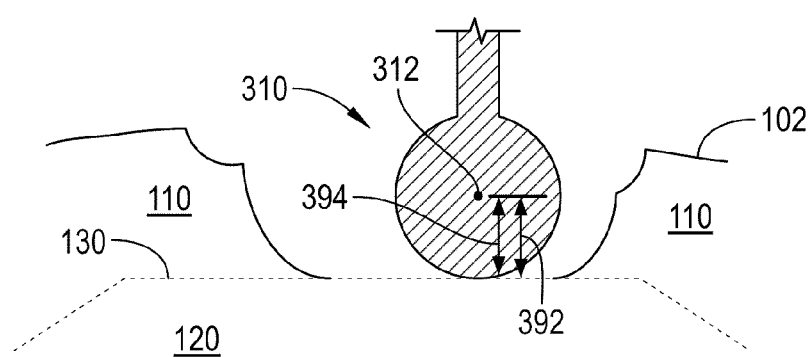
Figure 19:
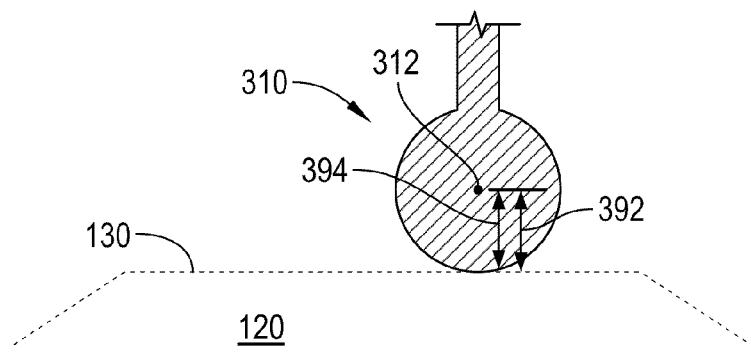

FIGS. 15-19 graphically illustrate steps of making one or more pre-planned optimized resections 130'. After registration, the tool 300 is operated to turn, vibrate, or reciprocate the cutter 310. The cutter 310 is then plunged into and through the anatomical surface 102 (e.g., articular surface) to remove portions 110 of bone, cartilage, and other anatomy between the cutter 310 and the one or more pre-planned optimized resections 130'. Realtime data regarding the spatial position 394 of the cutter 310 (e.g., center 312) relative to anatomy 102, 110 and one or more planned resections 130 is tracked via a tracking receiver 1010 and fed into a controller associated with computer 1020. When a surface of the cutter 310 approaches, meets, or exceeds a surface boundary of the one or more pre-planned optimized resections 130, the controller signals the tool 300 to retract the cutter 310 within the tool 300 or stop rotation of the cutter 310 so as to prevent cutting beyond the one or more preoperatively planned and optimized resections 130 as shown in FIG. 18. Alternatively, a display can warn the surgeon to reduce pressure or cutting in certain areas as the cutter 310 approaches, meets, or exceeds a surface boundary of the one or more pre-planned optimized resections 130.

At the point in time during surgery when the closest distance 392 between the cutter center 312 and the one or more planned resections 130 equals the radius of the cutter 310 for the entire boundary surface of the one or more planned resections 130, the step of modifying anatomy is finished, and the tool 300 can be removed from the surgical site. Thereafter, an implant 500 having attachment surfaces 534 matching the corresponding one or more planned resection surfaces 130 may be implanted.

Figure 20:
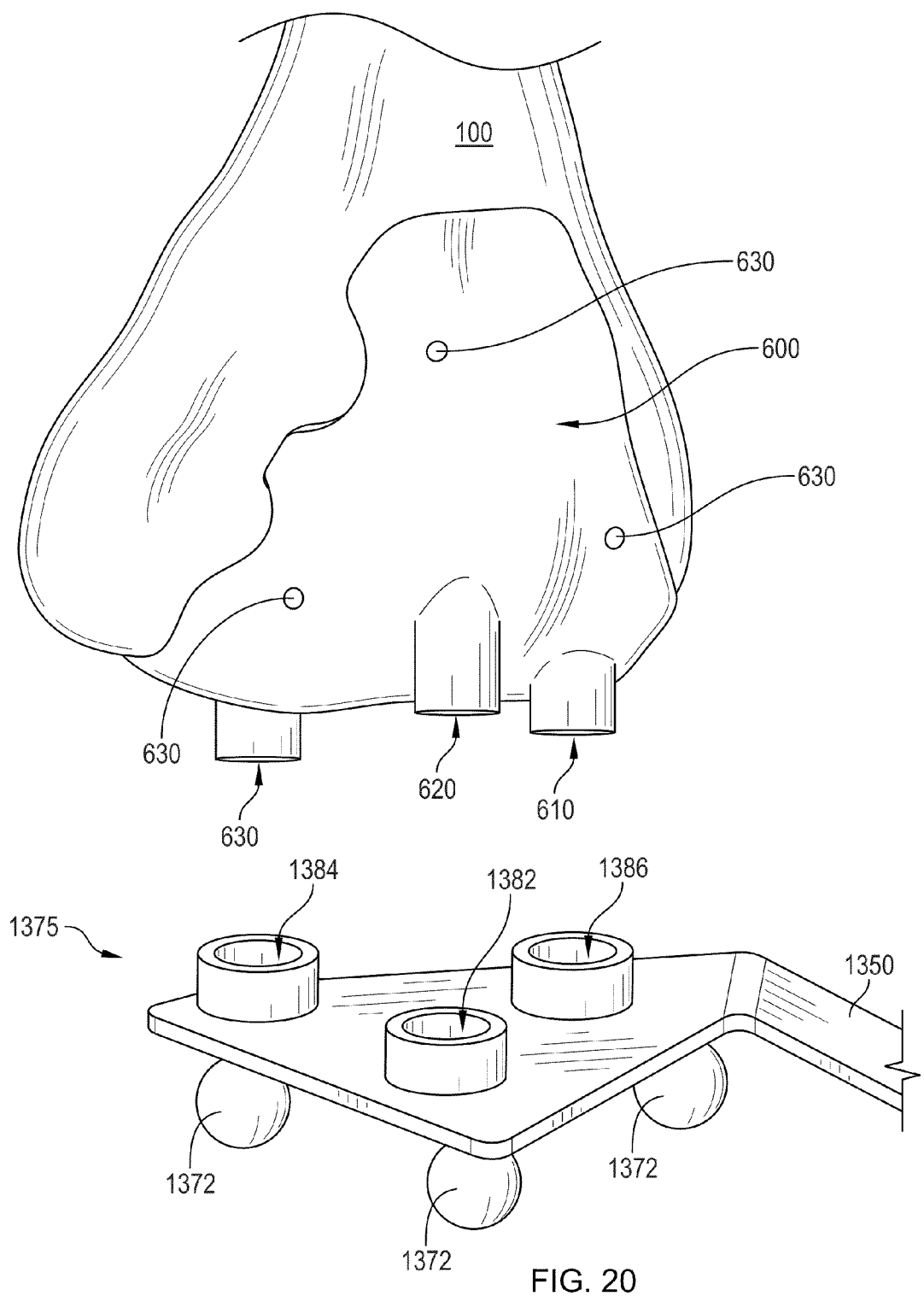
FIG. 20 shows registration features of a surgical system according to some embodiments.
Figure 21A:
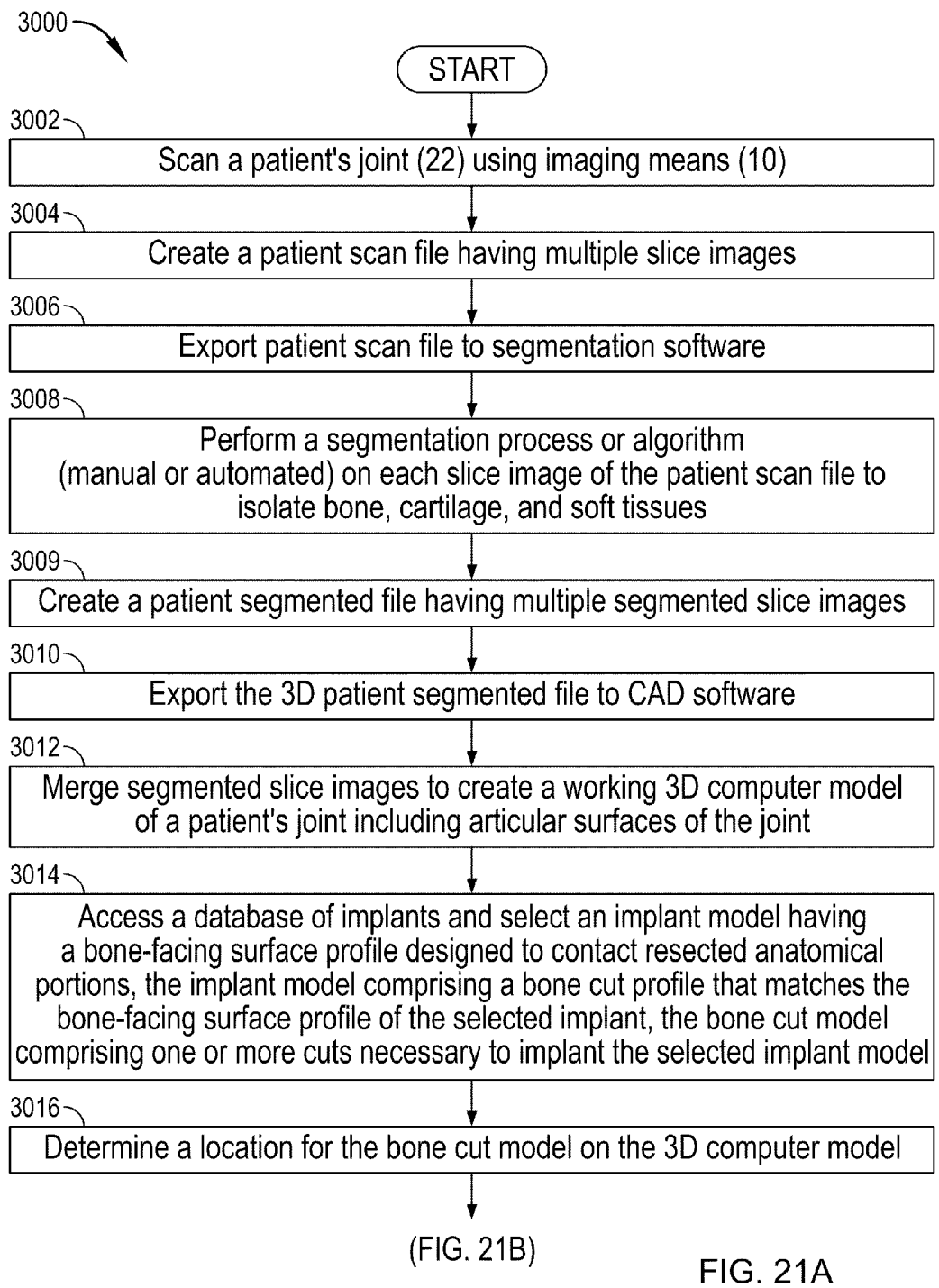
Figure 21B:
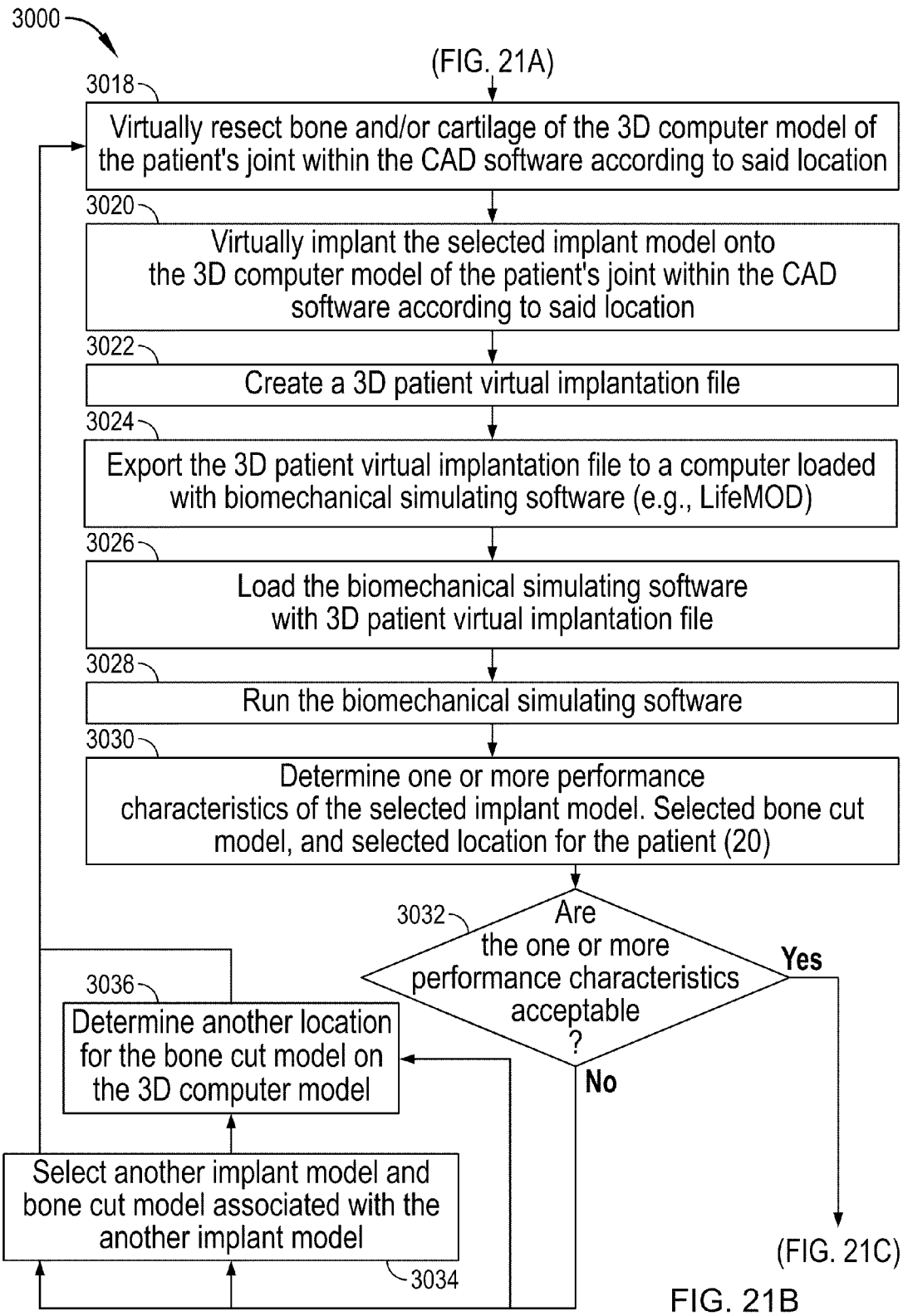
Figure 21C:
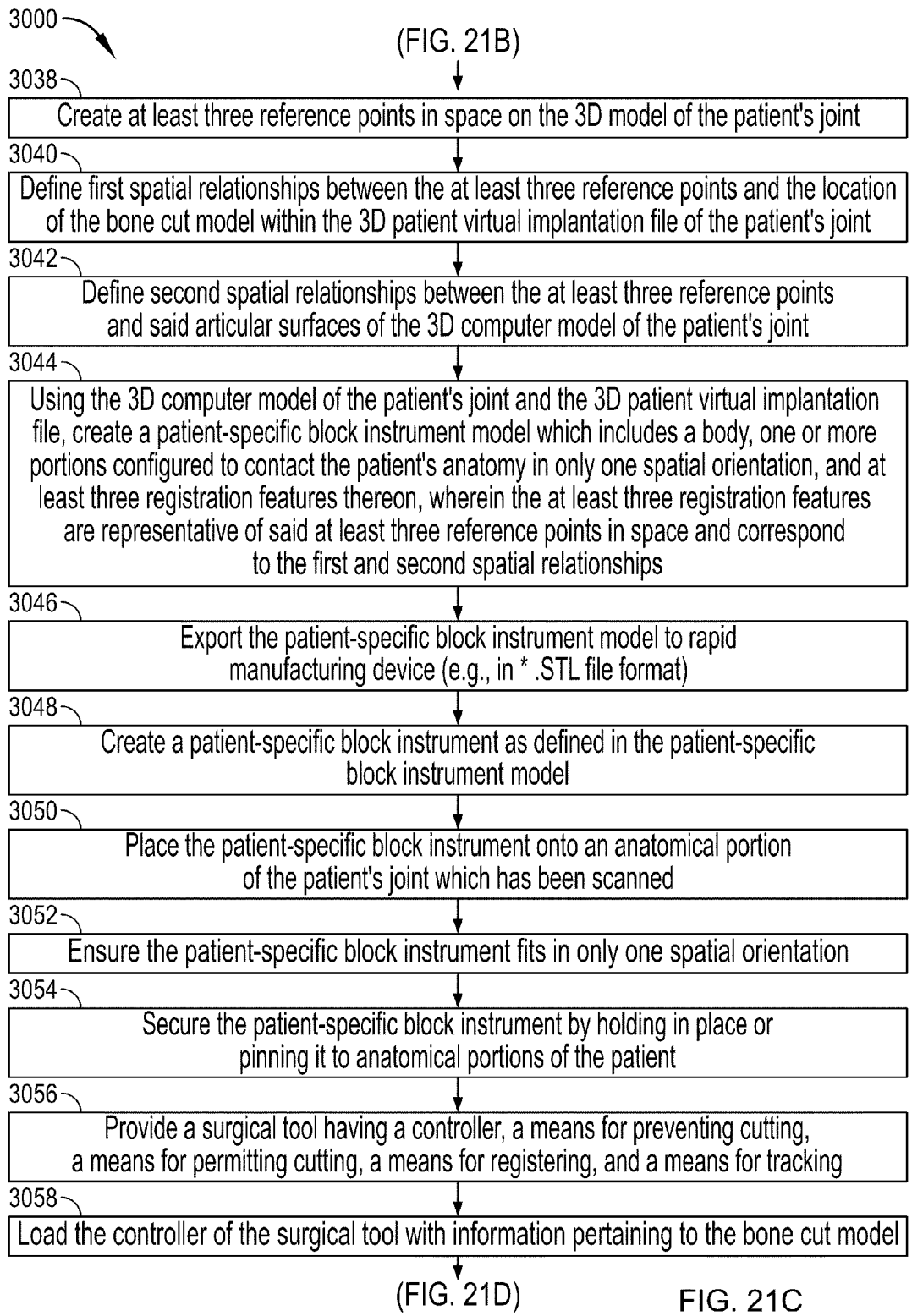
Figure 22:
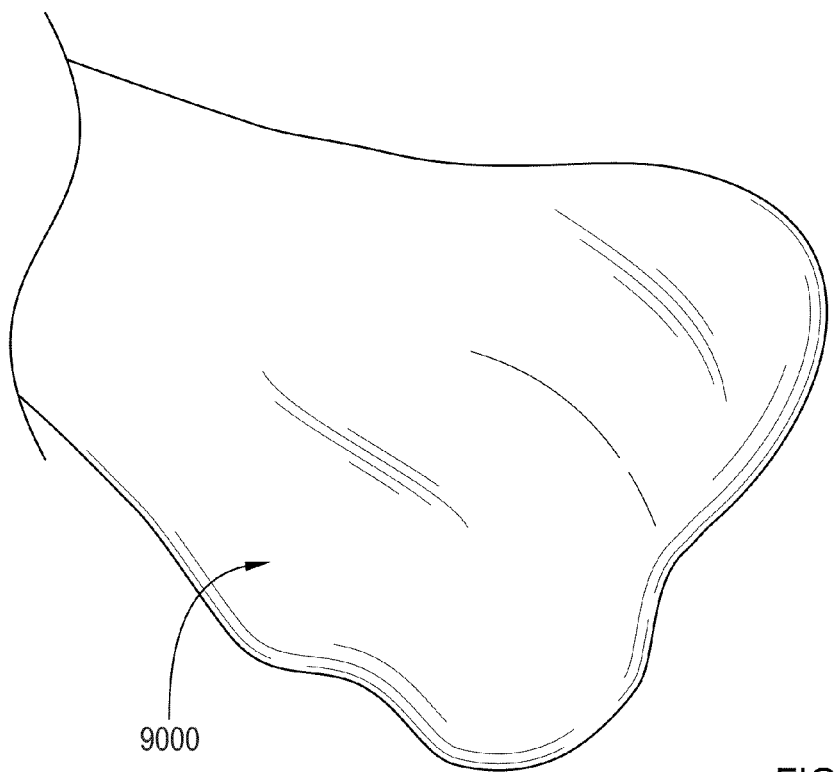
FIGS. 22-42 illustrate a surgical system and its use according to certain embodiments.

FIG. 20 illustrates an alternative apparatus and method for registration of surgical tools according to some embodiments. Surgical tool 300 comprises an array 1375 attached thereto via mounting means 1350. The array 1375 comprises at least three fiducial tracking markers 1372 similar to the embodiment shown in FIGS. 11, 14, and 15. However, the array further comprises a plurality of location features 1382 provided thereon which are adapted to communicate with a plurality of location features 610, 620, 630 provided on a patient-matched block 600. In certain embodiments, the location features 1382, 1384, and 1386 are shaped and contoured such that when the array 1375 joins the block 600, the inner and/or outer surfaces of the location features 1382, 1384, 1386 interfit with the location features 610, 620, 630 of the block 600 in only one orientation. In some embodiments, the location features are keyed to force the array 1375 to be positioned in one orientation only when the array 1375 engages the block 600. The location features 1382, 1384, 1386 may be held in place within the location features 610, 620, 630 by friction. In use, after the block 600 is secured to the anatomy 100 (e.g., by pinning the block 600 using holes 630), the location features on the array 1375 may be joined with the location features 610, 620, 630 on the block 600 in only one possible configuration. Then, the surgeon instructs the computer 1020 to register the spatial position and orientation of the tool 300. Because the dimensions of the cutter 310 for attachment to the tool is known and the cutter 310 may only be attached to the tool in one configuration, and the distance between each tracking fiducial marker 1372 and the center 312 of the cutter 310 can be determined, the computer 1020 can track the spatial orientation of the cutter 310 during a surgical procedure in real time.

FIGS. 21a-21d graphically illustrate a method of performing surgery 3000 according to some embodiments. A patient is scanned 3002 using imaging means such as CT, microCT, or MRI. Then, 2D image slices are saved 3004 and exported 3006 to segmentation software (e.g., MIMICS software). One or more portions of one or more of the image slices may be segmented 3008 in order to separate soft tissues from bone and cartilage. The resulting segmented 2D image slices may be combined 3009, 3012 into a single 3D file using software (e.g., MIMICS) and exported to CAD software 3010 to create a 3D patient model 50 for analysis and preoperative planning. The CAD software may also serve to smooth the single 3D file created from the segmented 2D image slices.

In certain embodiments, a custom implant and custom anatomical modification 130 is created based on the patient model 50, or an ideal implant 530 may be selected 3014 from a database 500 of implants 510, 520, 530. A computer model of the custom or selected implant, including attachment surfaces is loaded into the patient model, and positioned on the patient model in a first location and orientation 3016 via a virtual resection 3018 and virtual implantation 3020, 3022 as shown in FIGS. 7 and 8. In certain embodiments, the implant size is determined by fitting a trial implant for confirming the fit and sizing of an implant to be used. Optionally, biomechanical simulation software such as KNEESIM or LIFEMOD may then be used 3024, 3026, 3028 to determine one or more performance characteristics of the selected implant 530 if it is used on the patient 20 and oriented in the first location and orientation 3016 within the virtual 3D patient model 50 as shown in FIG. 9. If one or more of the performance characteristics are acceptable 3032, then a patient-matched block 200 may be created. If one or more of the performance characteristics of the selected implant 530 are not acceptable, then another implant 510, 520 may be selected 3034 from the database 500, or the same implant 530 may be virtually implanted 3036 in a second location and orientation using different virtual anatomical modifications 62, 63, and the simulation model 80 may be run again. In some embodiments, the proposed computer model and/or data relating to the performance characteristics may be sent electronically to a health care provider. In other embodiments, a network access may be provided to allow a health care provider to access via a computer and/or network the proposed computer model and/or data relating to performance characteristics. In some embodiments, a user, such as an engineer, may act upon instructions or approval received from a health care provider relating to the proposed computer model and/or data relating to the performance characteristics. If approval is denied, then a message indicating disapproval is sent via the network or the computer model and modifications are made to the model or data, and re-sent.

Steps 3038-3048 describe creating a patient-matched block 200 having registration features 210, 212, 214, 240, 242, 244. The registration features define registration points 211, 213, 215, 241, 243, 245 which are designed to receive and detect a location of a material removal implement, burr, bit, router, mill, or cutter 310 of a surgical tool 300 relative to a patient's anatomy 100 during surgery. Spatial relationships between registration points, articular surfaces 102, and one or more pre-planned optimized resections 130 are pre-defined, stored into a computer file, and uploaded into a computer 1020 having a controller. The computer file is used to manufacture the block 200, and may also be used during surgery to register in space, the relative spatial locations of the block 200, tool 300, cutter 310, articular surface 102, and all pre-planned anatomical modifications and resection profiles 130.

The surgeon places 3050 the patient-matched block 200 onto the affected site 100 (e.g., arthritic bone) so that it fits in only one spatial orientation 3052. The block 200 may be secured 3054 to the affected site 100 (e.g., with pins) so that a surgical tool 300 may be registered accurately with a computer-assisted surgery (CAS) system. The tool 300 provided in step 3056 may be registered by placing 3060, 3062 a portion of the tool (e.g., cutter 310) into each registration portion and simultaneously communicating 3064 information regarding the location of the surgical tool 300 to a computer 1020 while the surgical tool 300 is positioned at each registration portion of the block 200. The center location 312 of the cutter 310 at each registration portion 211, 213, 215, 241, 243, 245 generally matches identical spatial reference points 69a-f within an electronic file containing one or more preoperatively-planned patient-optimized anatomical modifications to be made 130' (See FIG. 7). In step 3058, the electronic file is uploaded to the computer 1020, and registration information is processed 3068 with the electronic file to define 3070 a surgical cutting boundary and set control limits for the surgical tool 300. Information relating to the surgical cutting boundary 130' is sent to a controller associated with the computer 1020. Tracking device 1010 determines real-time positioning of the tool 300 and cutter 310 and sends information regarding instant tool position to the controller. The tracking device 1010 may be a passive or active system. The system may utilize electromagnetic waves, infra-red, or ultrasound. In certain embodiments, the system is passive and uses infra-red. If the real-time position and orientation of the tool 300 places the cutter 310 shallower than the desired cutting boundary 130', then the controller instructs the tool 300 to continue cutting 3072. However, if the real-time position of the tool 300 places the cutter 310 adjacent to, on, or past the desired cutting boundary 130', then the controller instructs 3074 the tool 300 to discontinue continue the cutting operation. For instance, the controller may instruct the tool 300 to retract the cutter 310 or reduce or eliminate current to the tool 300 when the computer-assisted tracking software determines that the cutter 310 is adjacent to, on, or past the desired cutting boundary 130'.

Once the anatomy is prepared 3076, an implant 530 having attachment surfaces 534 matching the prepared anatomy 130 may be installed 3078, and the surgical procedure is finished 3080 in a conventional manner.

FIGS. 22-43 illustrate an alternative surgical system and a method of its use. A patient-specific instrument is provided that is designed to conform at least in part to a contour of a patient's unique anatomy. For instance, as shown, a patient-specific instrument is provided as a distal femoral block 2000 comprising one or more mounting devices such as holes 2002, 2004, 2006 for receiving one or more surgical fasteners 2202, 2204, 2206. The block 2000 has an anatomy-facing portion 2020 that includes a surface contact, line contact, or point contact with the patient's anatomy 9000 (e.g., distal femoral articular cartilage and bone). The block 2000 mates with the anatomy 1000 in only one spatial orientation within six degrees-of-freedom. Block 2000 includes an alignment site in the form of an adapter portion 2100 that mates with a complementary adapter portion 2460 of a mount 2400. The housing receives an array or other imaging site, as discussed below, and thus the housing 2400 functions as a mount. The adapter portions 2100, 2460 may be structured as dovetail connections, tongue-in-groove connections, peg-in-hole connections, snap-fit connections, male/female connections, or any other known connections. The adapter portions may be self-securing or may be temporarily fixed together with one or more screws, magnets, or pins. Moreover, the adapter portions may be configured so that the mount 2400 can attach to the block 2000 from multiple directions.

Figure 24:
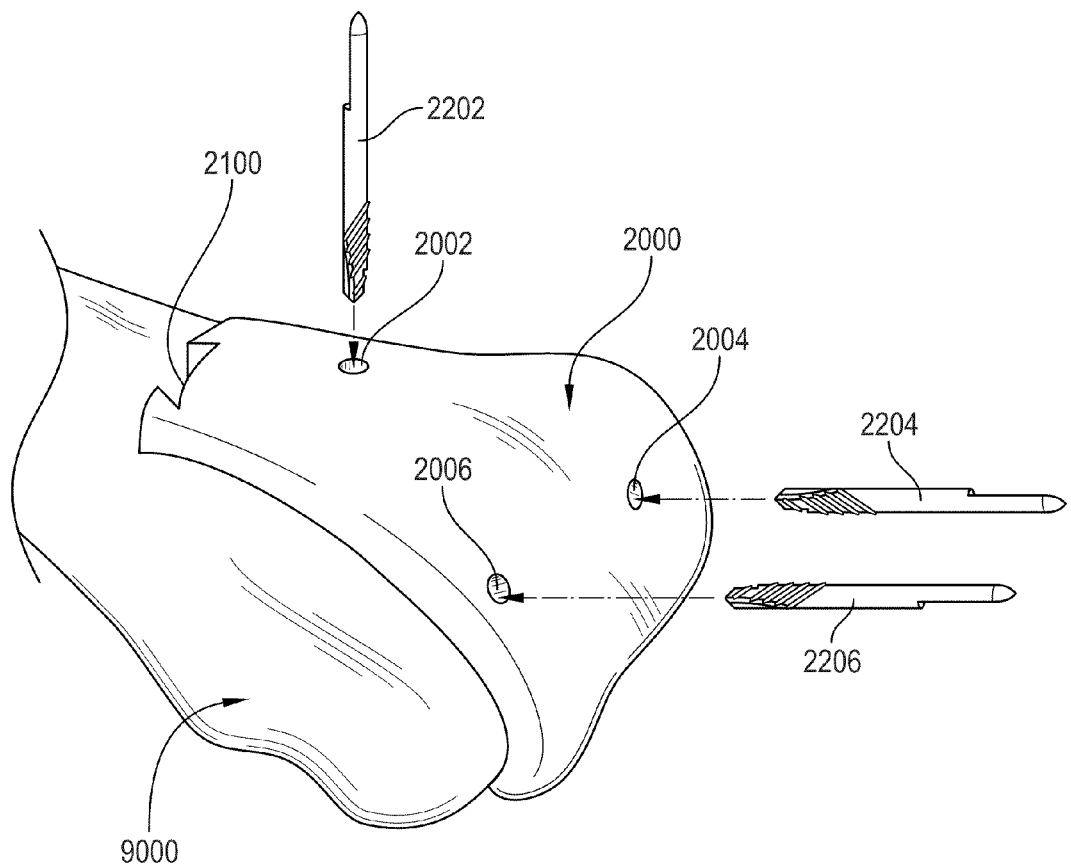
Figure 25:
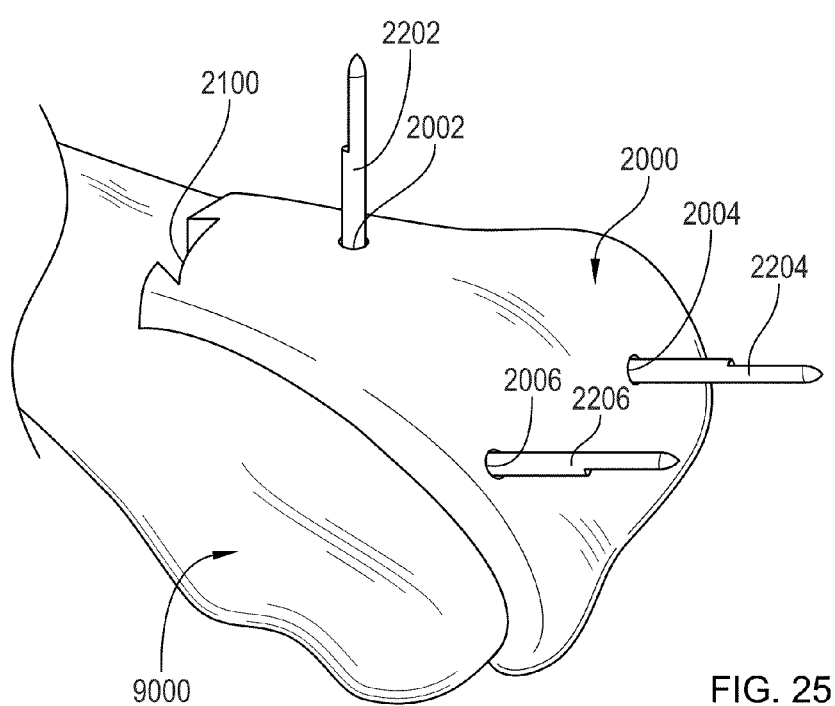
Figure 26:
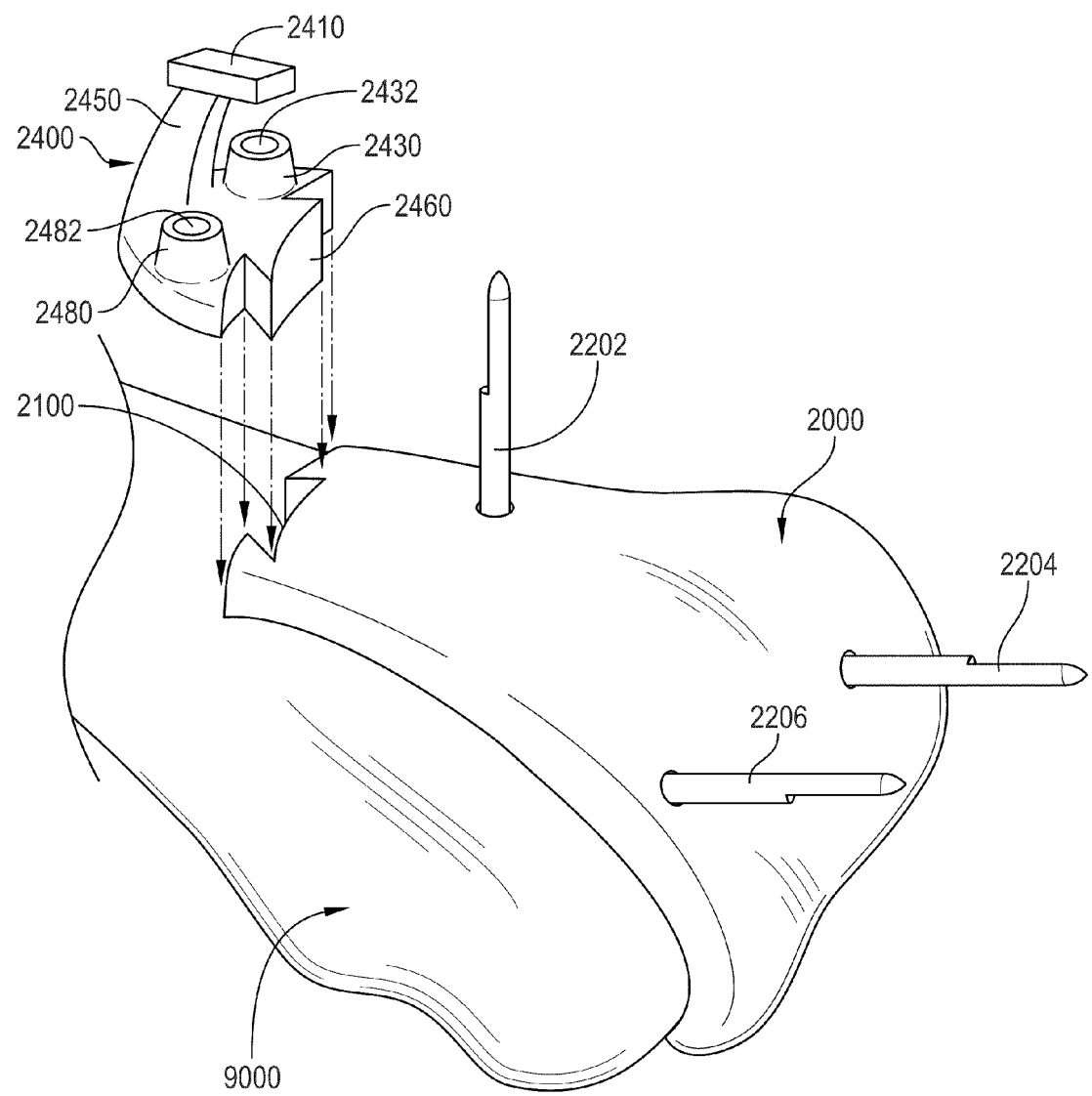
Figure 27:
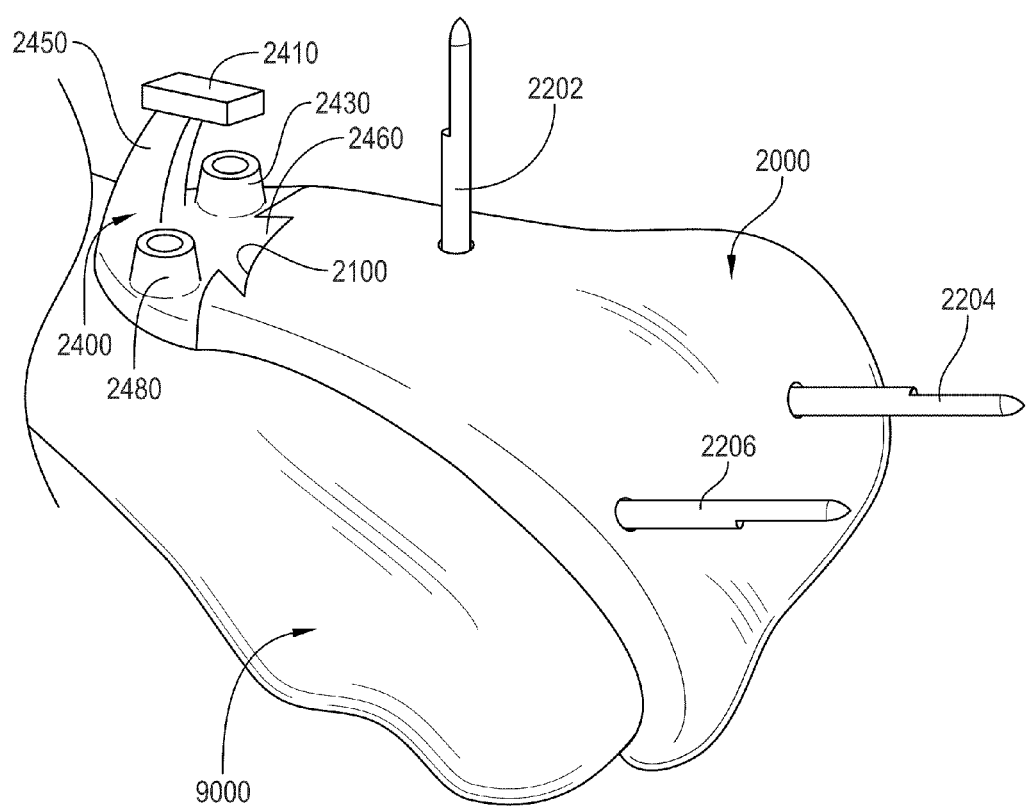
Figure 28:
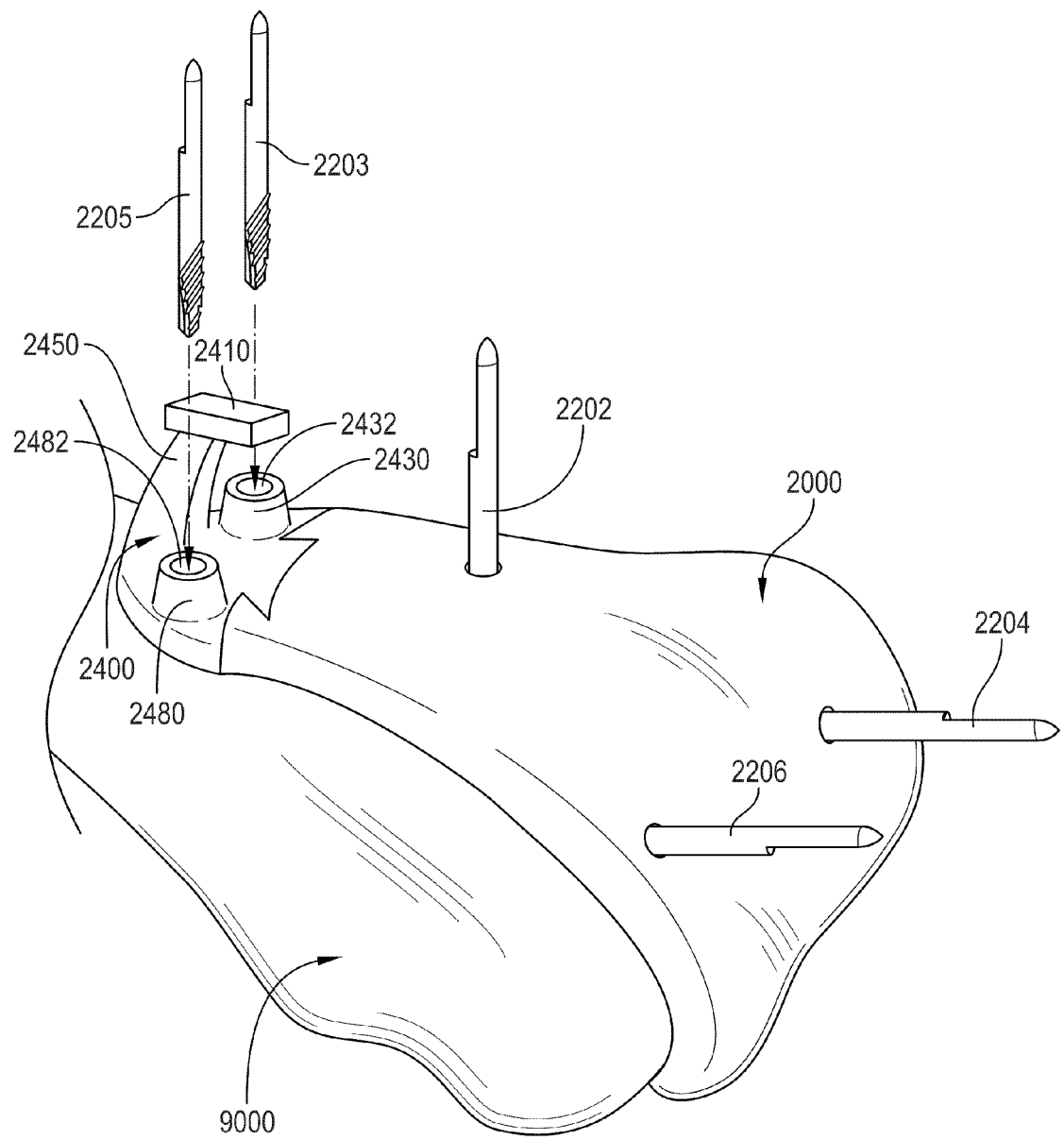
Figure 29:
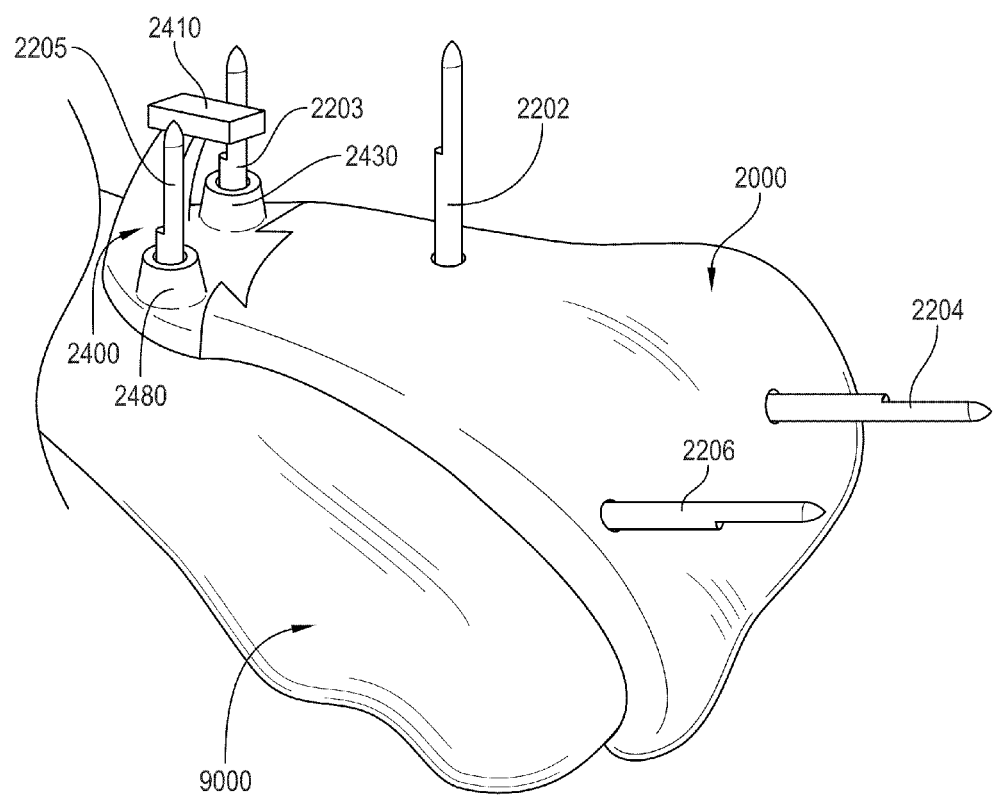
Figure 30:
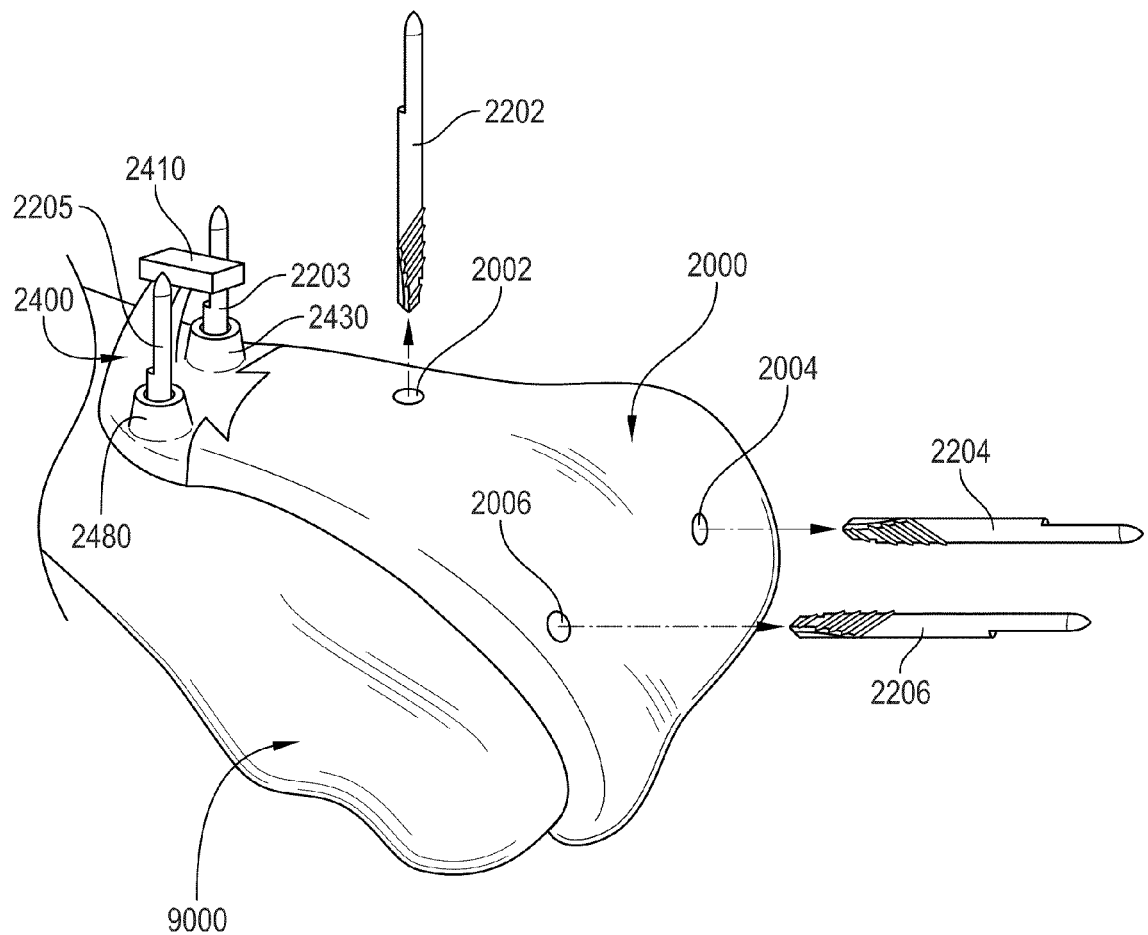
Figure 31:
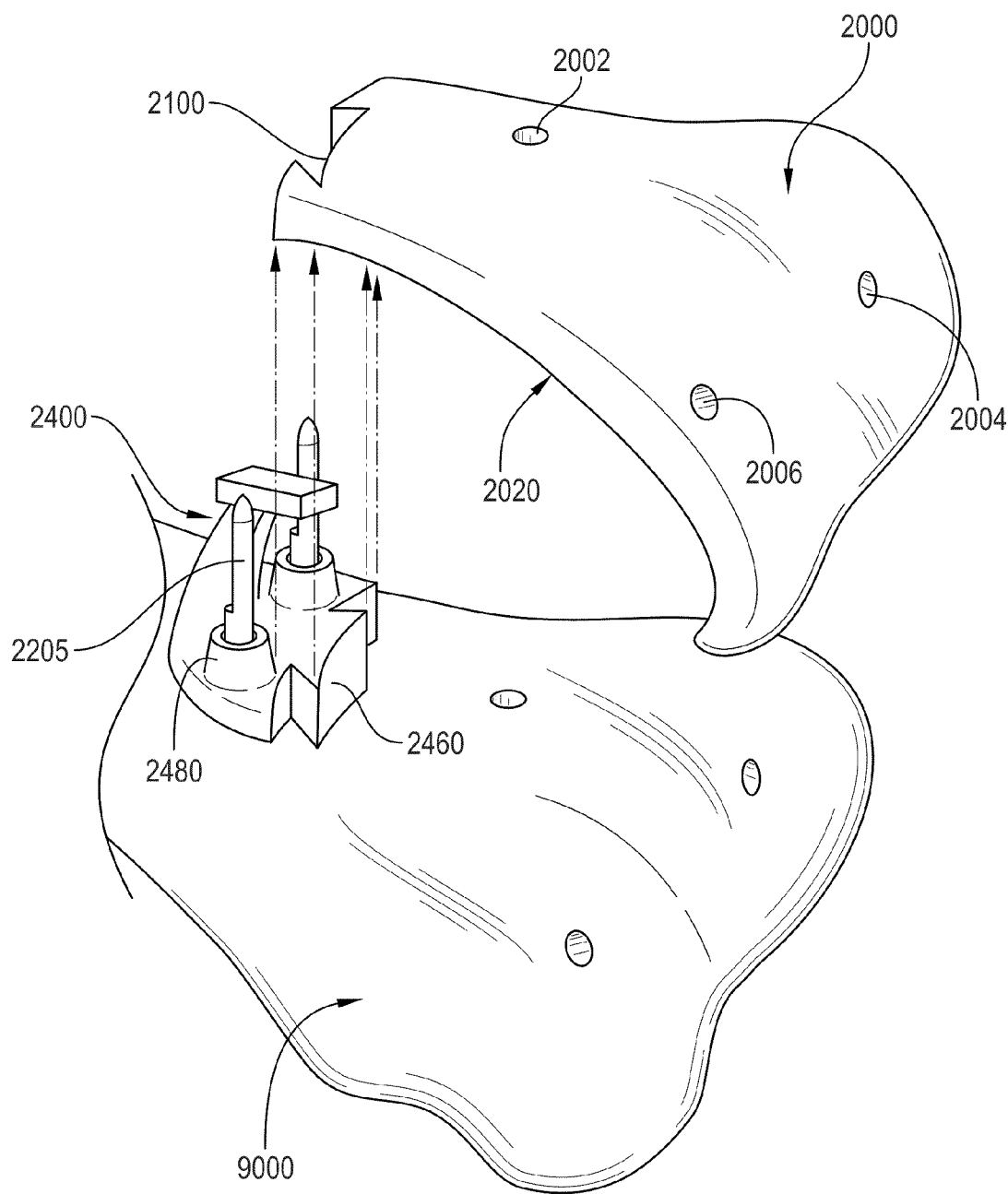
Figure 32:
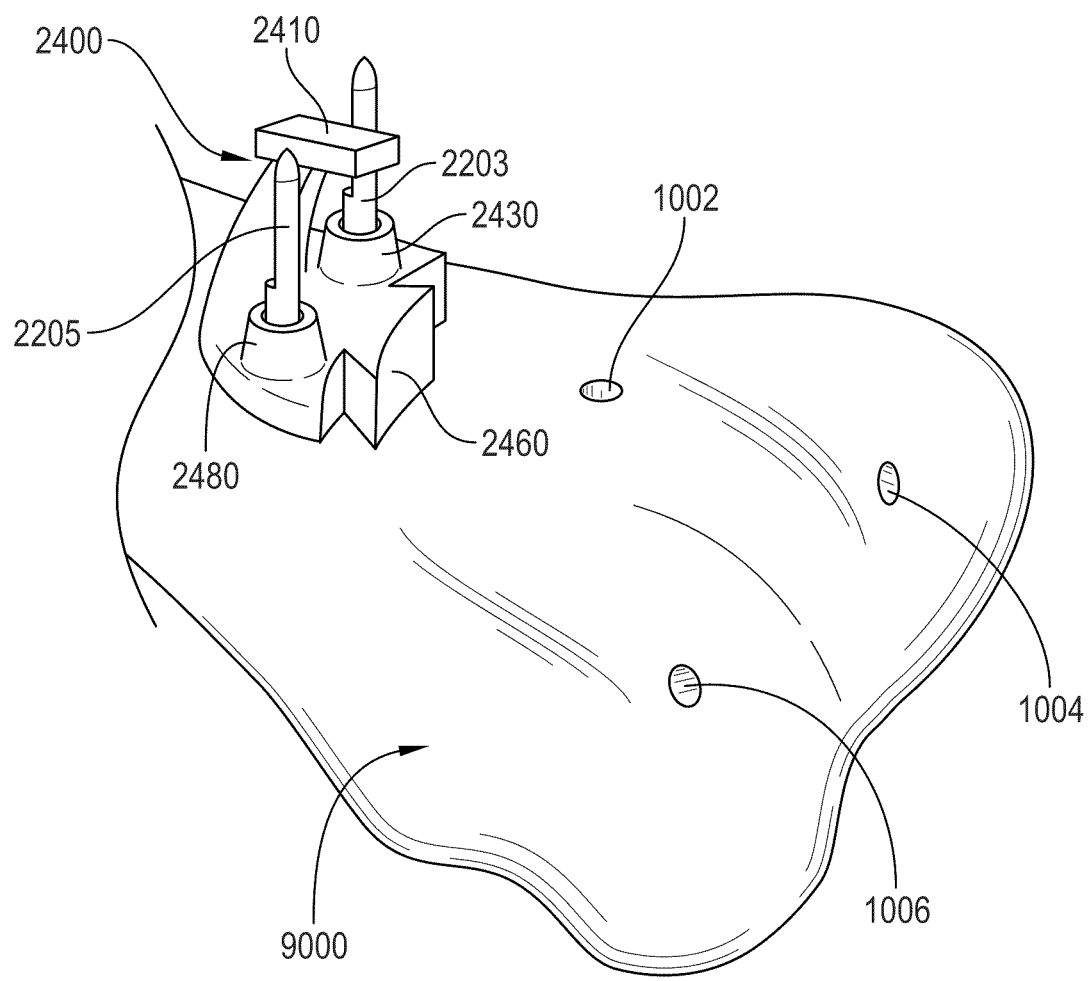

The block 2000 may be held to the patient's native anatomy, or secured thereto using surgical fasteners 2202, 2204, 2206 as shown in FIGS. 24 and 25. Mount 2400 may then be secured to the block 2000 via adapter portions 2460, 2100 as shown in FIGS. 26 and 27. The mount is then secured to the patient's anatomy as shown in FIGS. 28 and 29. For example, the mount 2400 may have one or more bosses 2430, 2480 having apertures 2432, 2482 therein which are suitable for receiving surgical fasteners 2203, 2205. Once mount 2400 is secured to the patient's anatomy, the block 2000 may be removed as shown in FIGS. 30 and 31. Small voids 9002, 9004, 9006 may exist where surgical fasteners 2202, 2204, 2206 are used.

Mount 2400 may comprise an extension portion 2450 and a mounting adapter for receiving an array 2500 having a complimentary mounting adapter 2510. The mounting adapters 2410, 2510 preferably rigidly secure the array 2500 to the mount 2400 in only one relative spatial orientation within six degrees-of-freedom. Once the array 2500 is fitted to the mount 2400, a location of the array 2500 is tracked and communicated to a processor of a computer assisted surgical system. Array generally comprises three or more fiducial markers 2502, 2504, 2506 visible to a receiver 1010 of a computer assisted surgical system which may be mounted to a platform 2518. Mounting adapters may comprise portions of tracks, threaded connections, dovetail joints, ball detents, snap-fit releasable connections, quarter-turn fasteners, or magnetized male/female connections.

During the creation of the block 2000, engineers strategically set the datum of the mounting adapter 2410 (and ultimately, the datum of the array 2500 and plane between markers 2502, 2504, 2506) to be in a fixed spatial relationship with respect to the conforming anatomy-facing surface profile 2020. In this way, the patient-matched block 2000 serves to perform an "instantaneous" registration function, without requiring the surgeon to participate in the time-consuming steps of touching a surgical tool to various anatomical landmarks as conventionally required. Moreover, the block 2000 allows an engineer or surgeon to actually replicate a preoperative surgical plan with more accuracy than conventional CAS methods, because the possibility of introducing error into the procedure from inaccurate manual registration techniques is eliminated. The datum established by the block positions the array 2500 at a known spatial orientation with respect to the patient's anatomy 9000.

Figure 35:
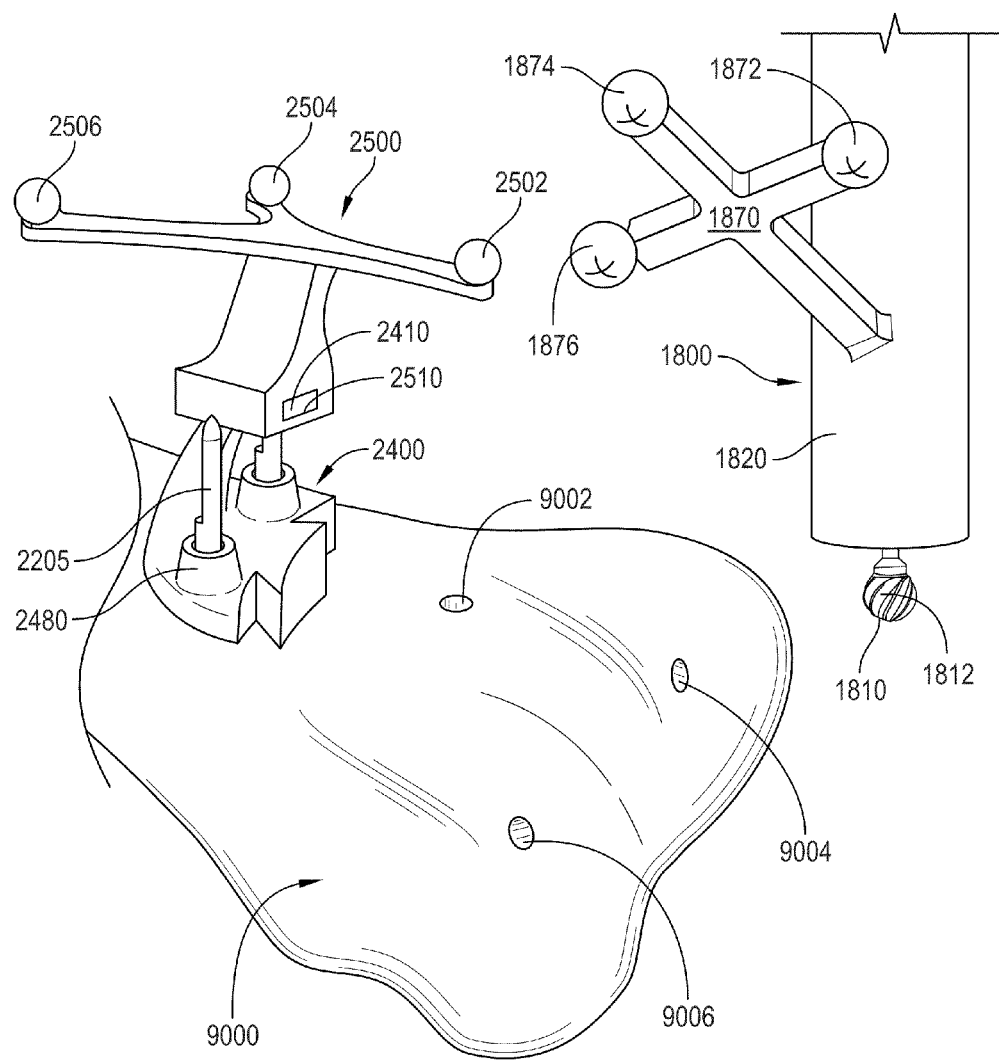
Figure 36:
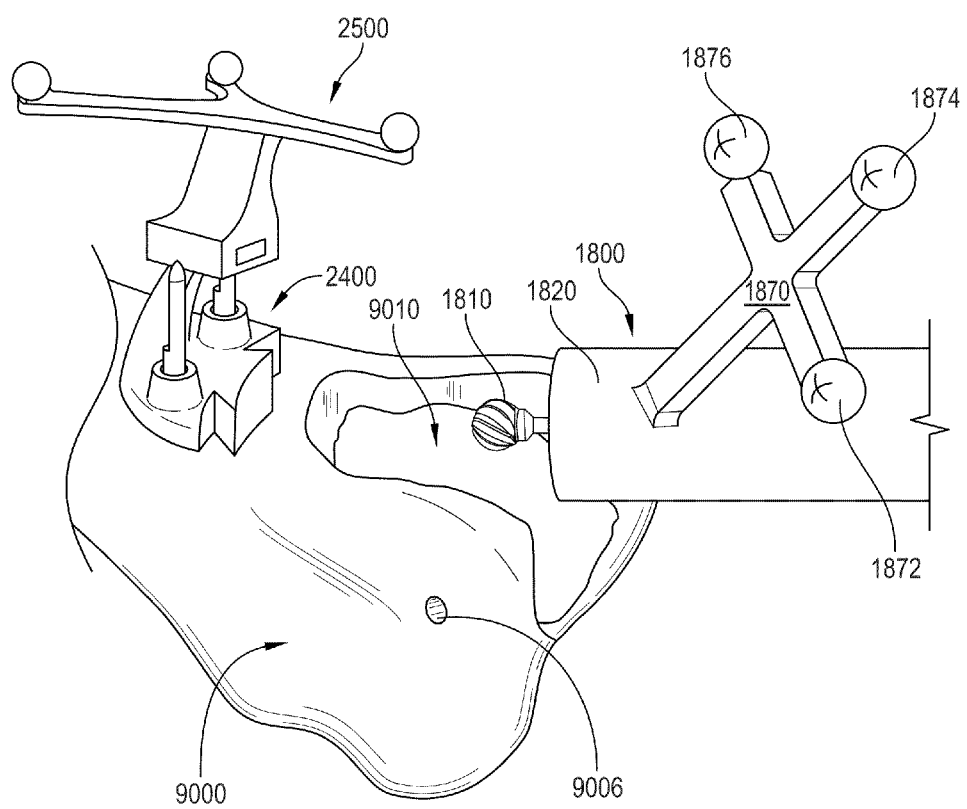
Figure 37:
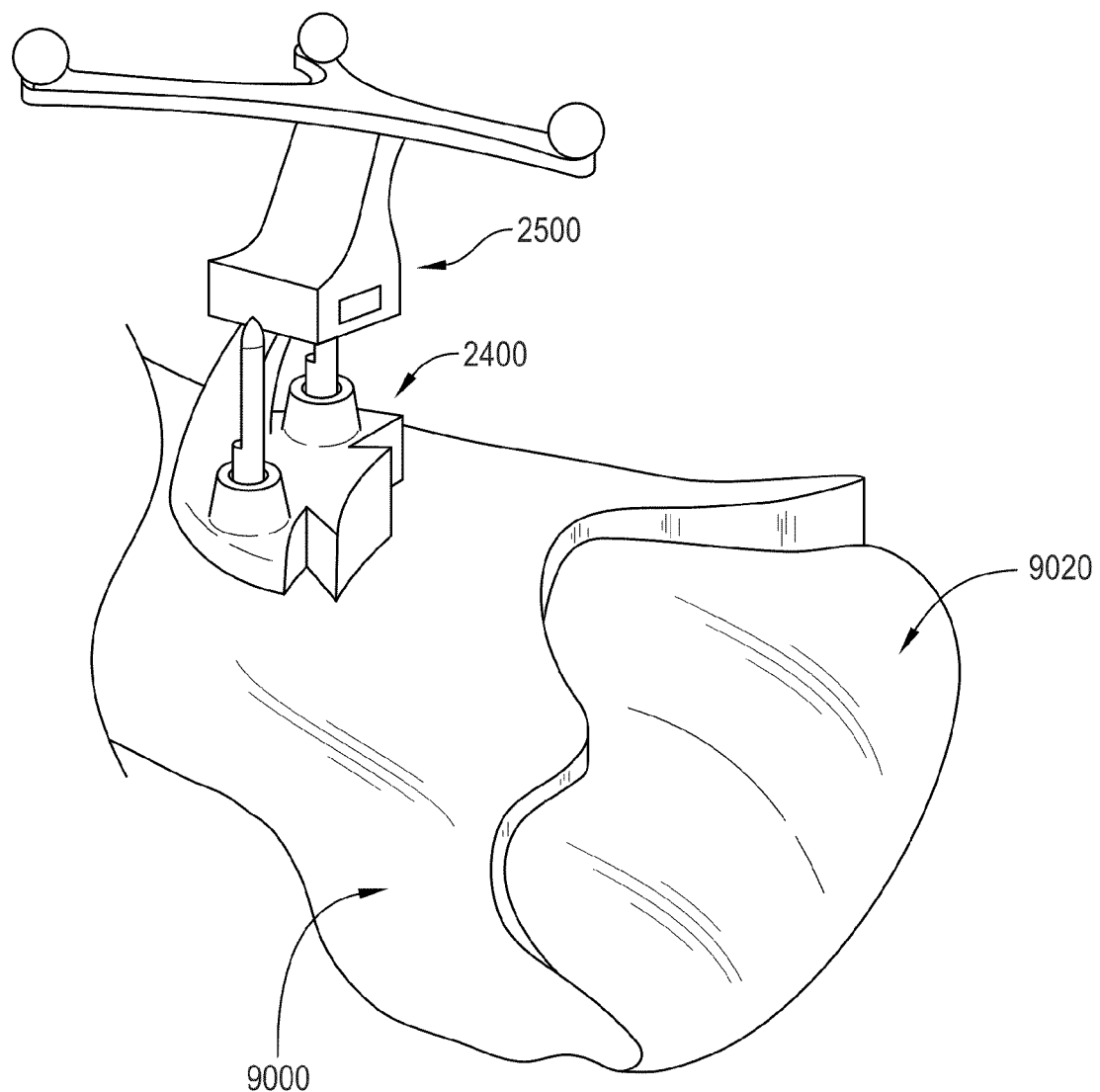

As shown in FIGS. 35-37, the surgical tool 1800 may be used to make one or more anatomical changes to the patient's anatomy 9000. For example, as shown, tool 1800 includes a body 1820, a tracking member 1870, and a cutter 1810. In certain embodiments, the cutter 1810 is rotable (e.g., a burr or end mill device) and is computer-controlled to assist the surgeon in making anatomical changes 9010, 9020 that closely match a preoperatively-defined surgical plan. The tracking member 1870 may be provided, for example, as an array having at least three fiducial markers 1872, 1874, 1876 which may be tracked in space by a receiver (e.g., receiver 1010 shown in FIG. 15). When the tool 1800 moves the cutter 1810 to a location of the anatomy 9000 that approaches a pre-defined resection boundary 130', a controller sends an input to the tool 1800 which provides a response from the tool 1800. The input may comprise, for example, removing current to the tool 1800 or instructing the tool 1800 to retract the cutter 1810, and the response from the tool 1800 may be, for instance, terminating further anatomical changes (e.g., stop cutting).

Figure 33:
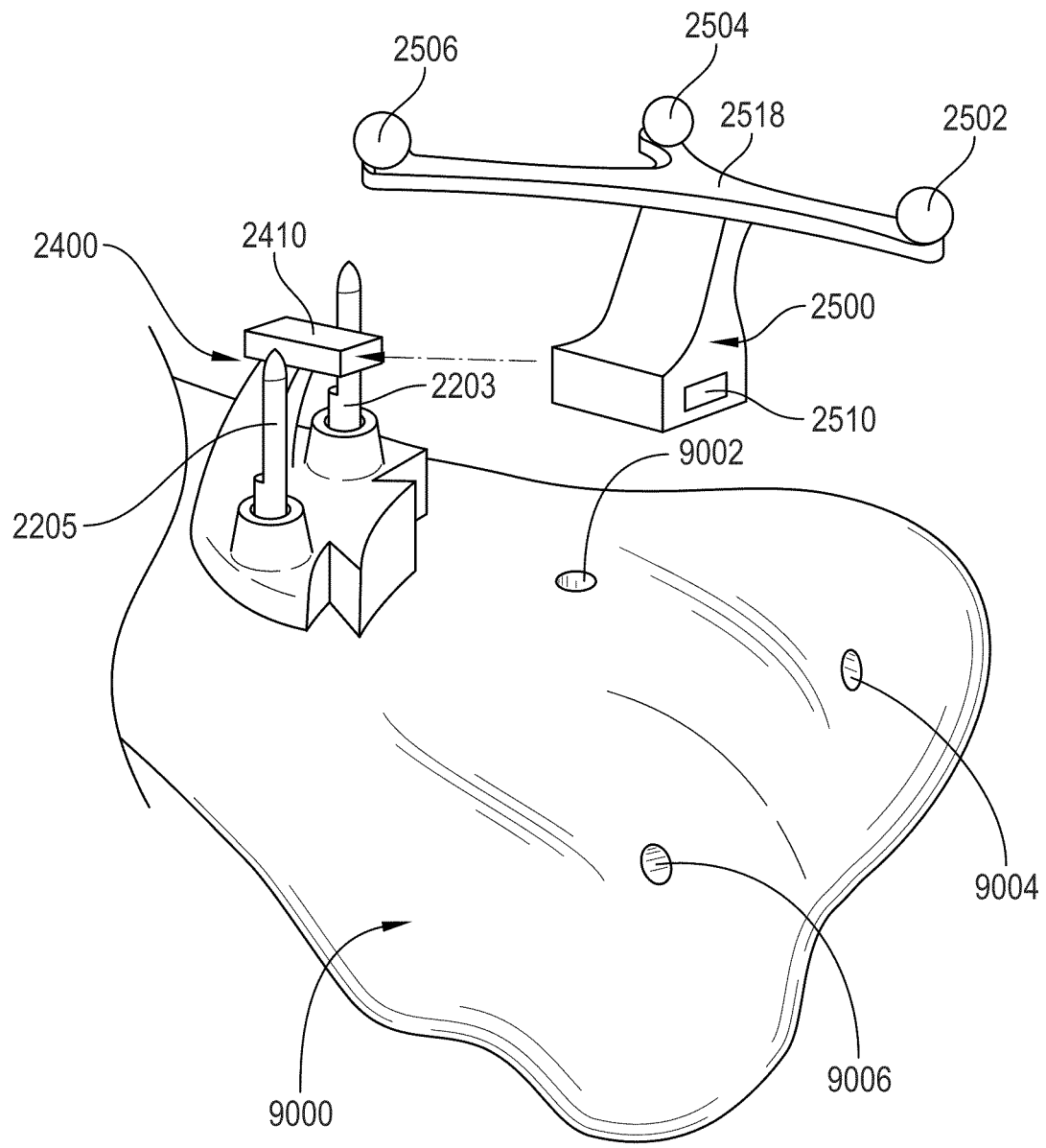
Figure 34:
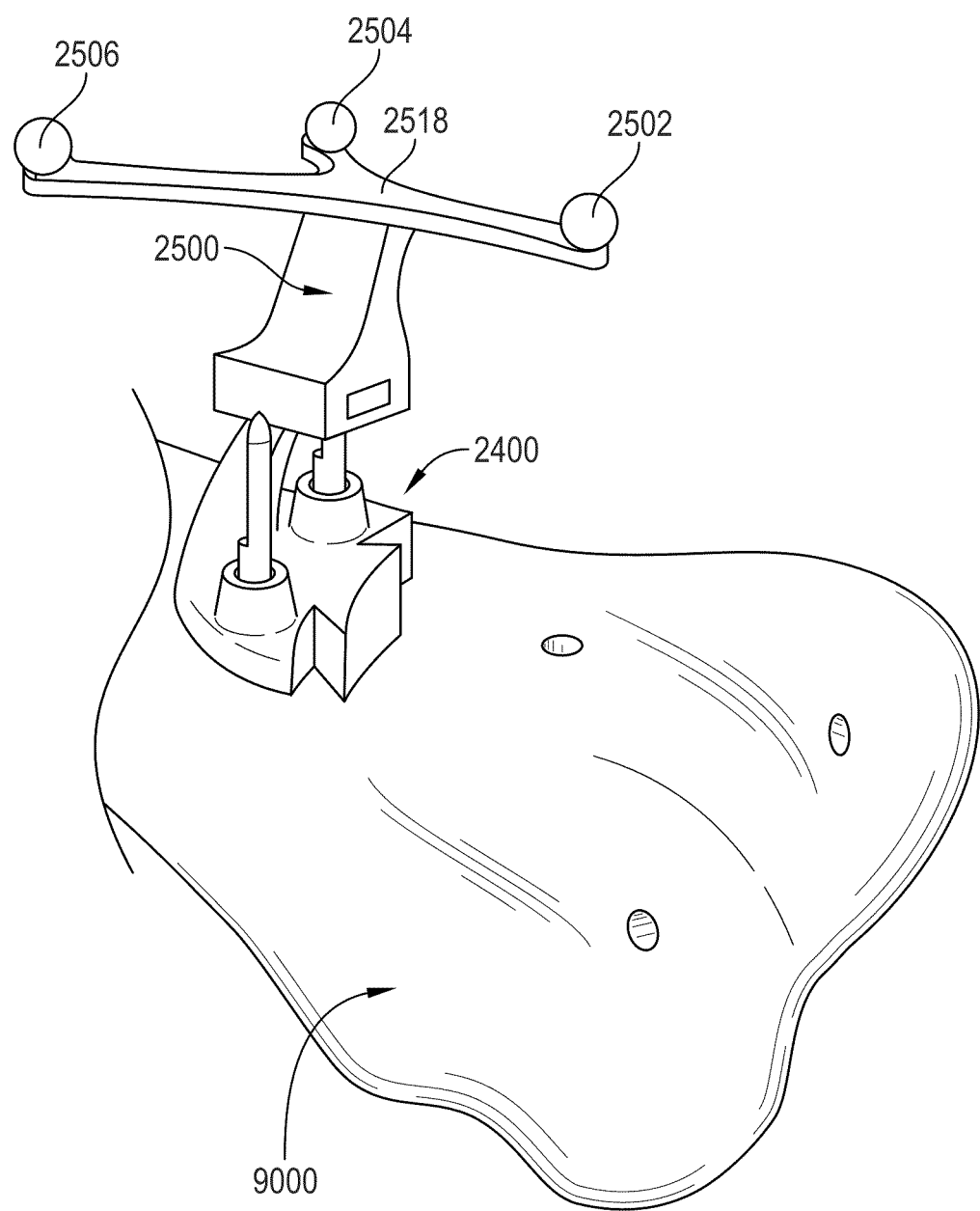

In the embodiments described above in FIGS. 11-14, the patient-matched block has one or more alignment sites (e.g., 210, 212, 214, 240, 242, and 244) that receives a registration tool (e.g., tip 310 of the surgical tool 300). The registration tool then joins the alignment sites and a location of the surgical tool is tracked with respect to the patient's bone by detecting the position of the surgical tool with respect to a reference array (e.g., 470) positioned near or on the patient. In such implementations, the surgical tool 300 functions as both the registration tool and the cutter, and the registration and re-registration occurs by touching the distal tip of the cutter to the registration sites on the block. In the alternative implementations of FIGS. 22-36, the registration tool houses the reference array and uses a single registration site (e.g., adaptor portion 2100). The housing 2400 (FIG. 26) is an example of such a registration tool. The housing 2400 connector (e.g., adaptor portion 2460) interfaces with a complimentarily shaped connector (e.g., the adaptor portion 2100 of the patient-matched block 2000 as shown in FIG. 26) to align with respect to the block. The housing adaptor 2410 receives the array 2500 as shown in FIG. 33. A location of the surgical tool such as a surgical tool 1800 (FIG. 36) can be tracked with respect to the patient's bone by detecting the position of the surgical tool with respect to the reference array 2500. In this case, the reference array 2500 is directly engaged to the housing 2400. Such implementation can eliminate the need to touch the site with the cutter for registration. The array mounted to the housing 2400 (aligned according to the patient-specific block) is registered by the processor, thereby automatically registering the location of the patient's bone.

Figure 38:
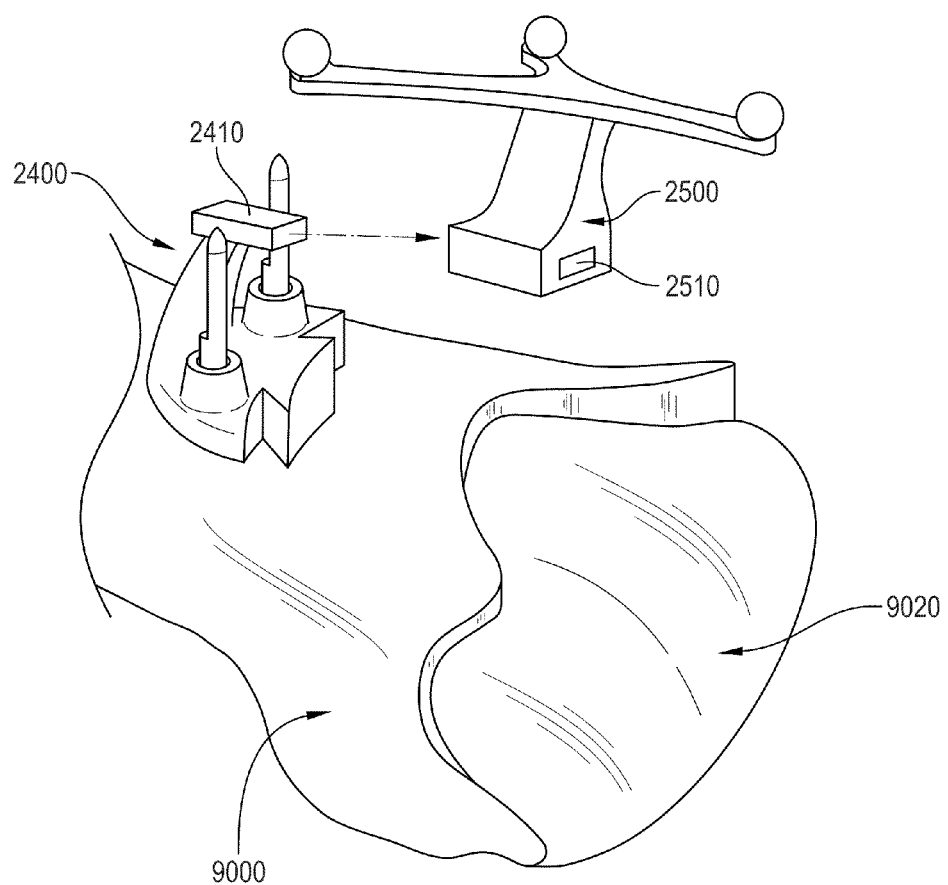
Figure 39:
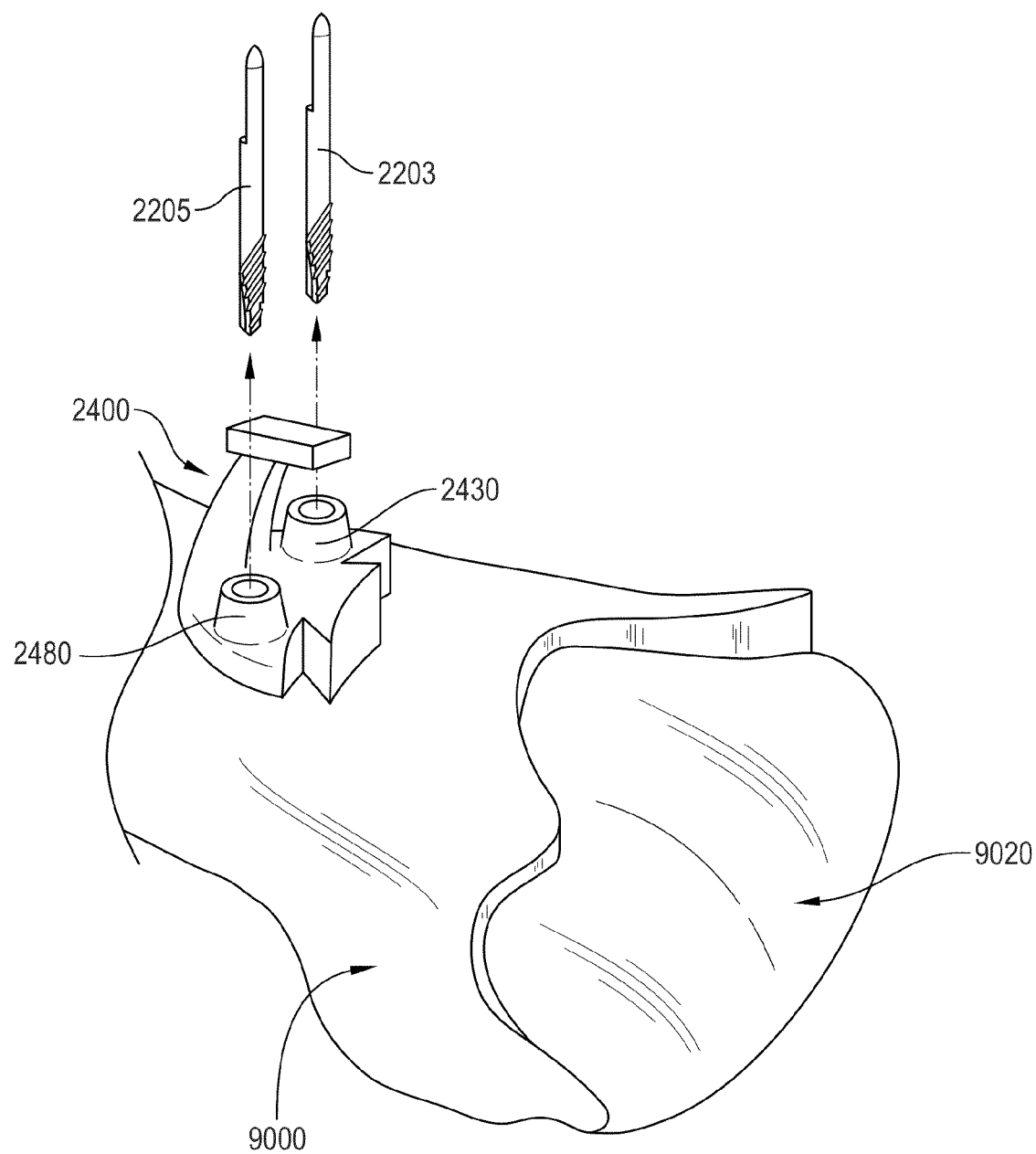
Figure 40:
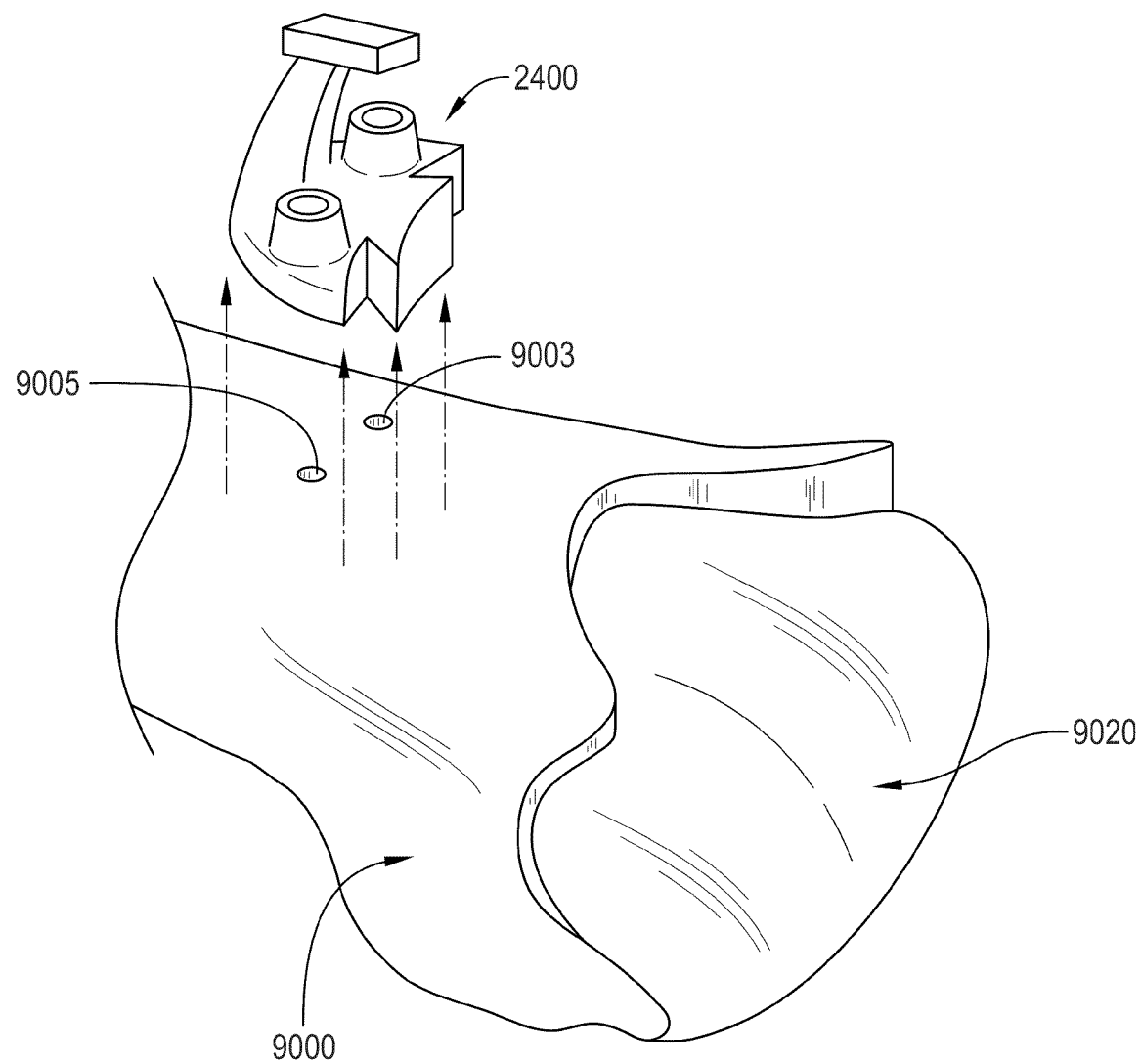
Figure 41:
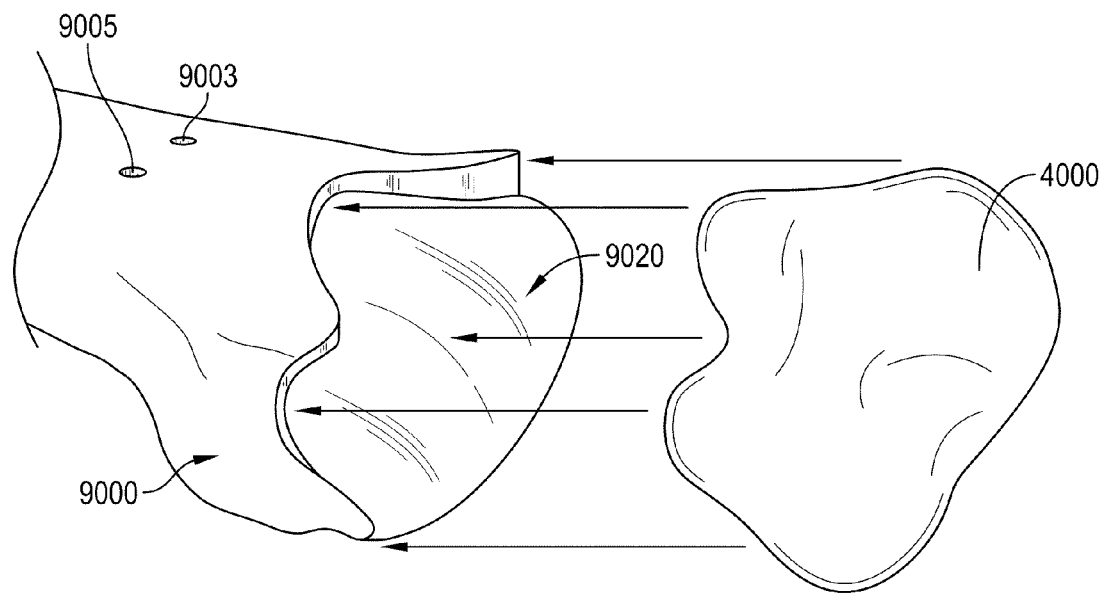
Figure 42:
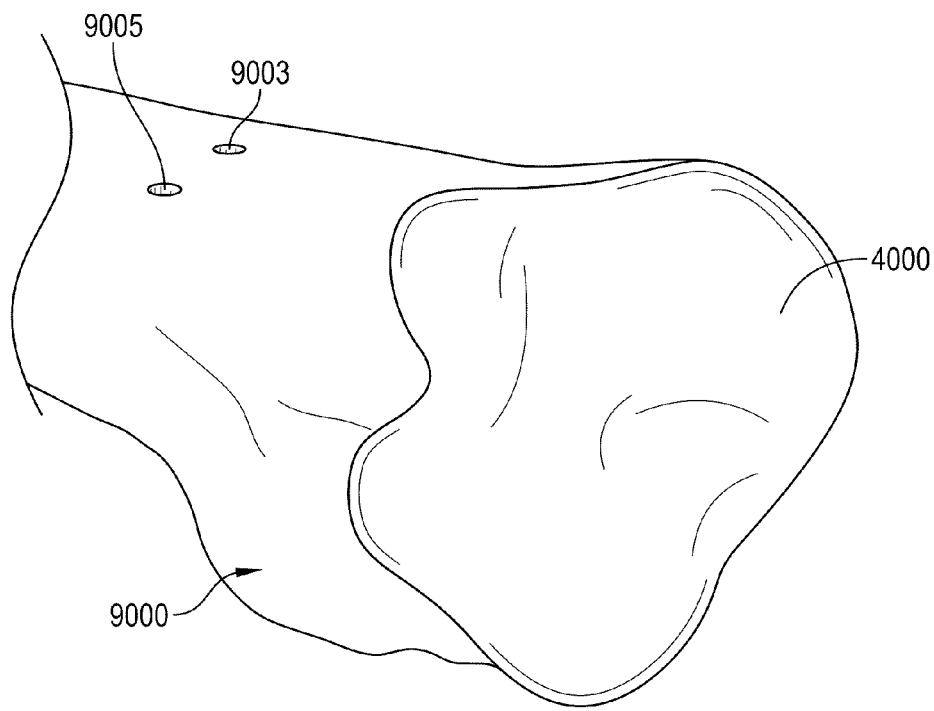

Once the actual anatomical modification 9020 substantially matches anatomical changes 130' outlined in the preoperatively-defined surgical plan, the array 2500 and mount 2400 may be removed from the anatomy 9000 as shown in FIGS. 38-40 so that an implant 4000 may be installed. Anatomical voids 9003, 9005 may be present where surgical fasteners 2203, 2205 are used to secure the mount 2400 to the patient's anatomy 9000. The implant 4000 may be a custom implant or standard implant. Anatomical modifications 9020 may optimize the placement of a standard implant in order to achieve best biomechanic performance for the patient. Implant 4000 may have an anatomic-facing portion (e.g., peg, keel, ridge, protuberance, porous ingrowth structure, or cement interface surface) that matches the anatomical modification 9020.

Figure 43:
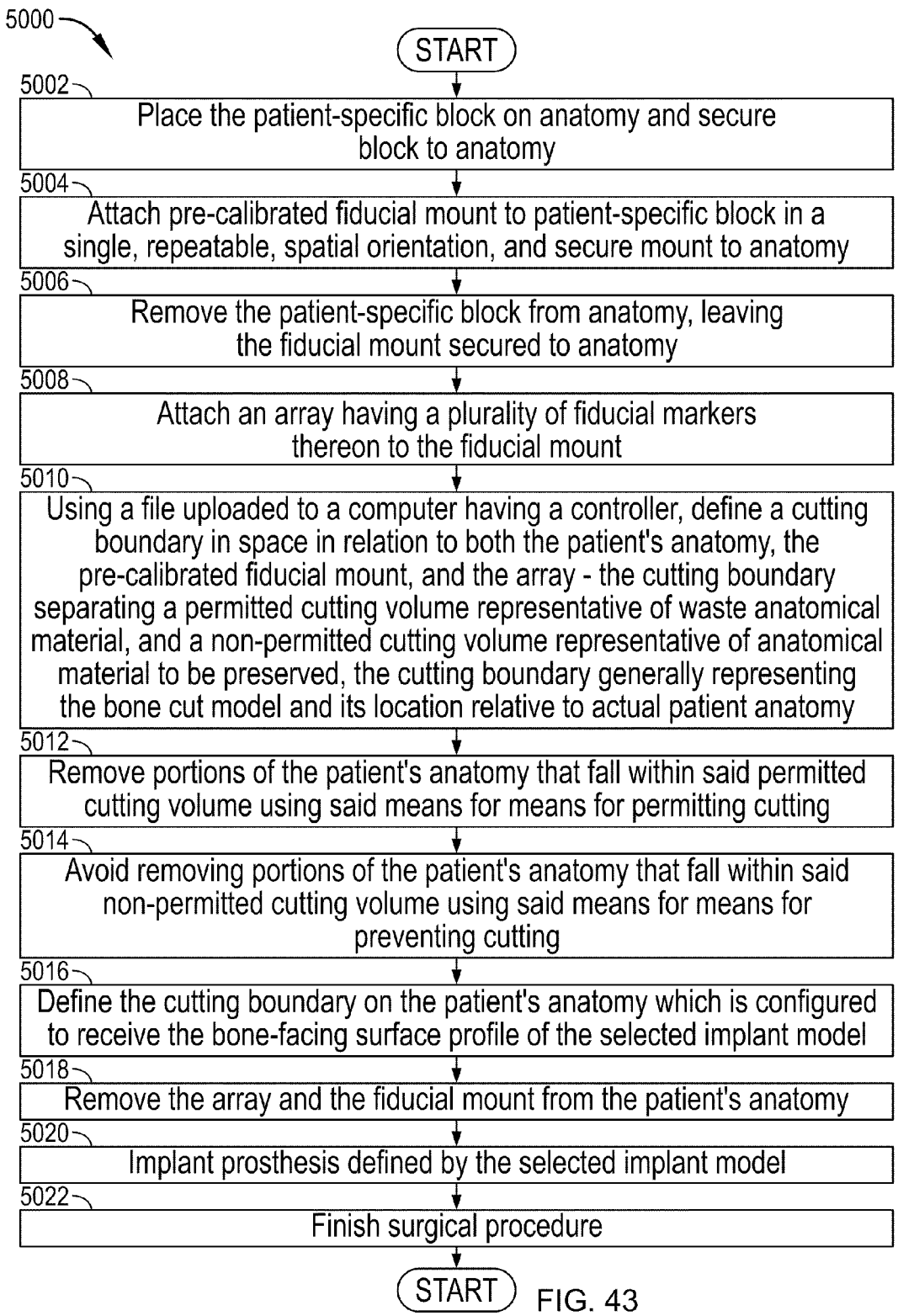
FIG. 43 schematically illustrates a method of using a surgical system shown in FIGS. 22-42.

FIG. 43 schematically illustrates the method illustrated in FIGS. 22-42.

Figure 44:
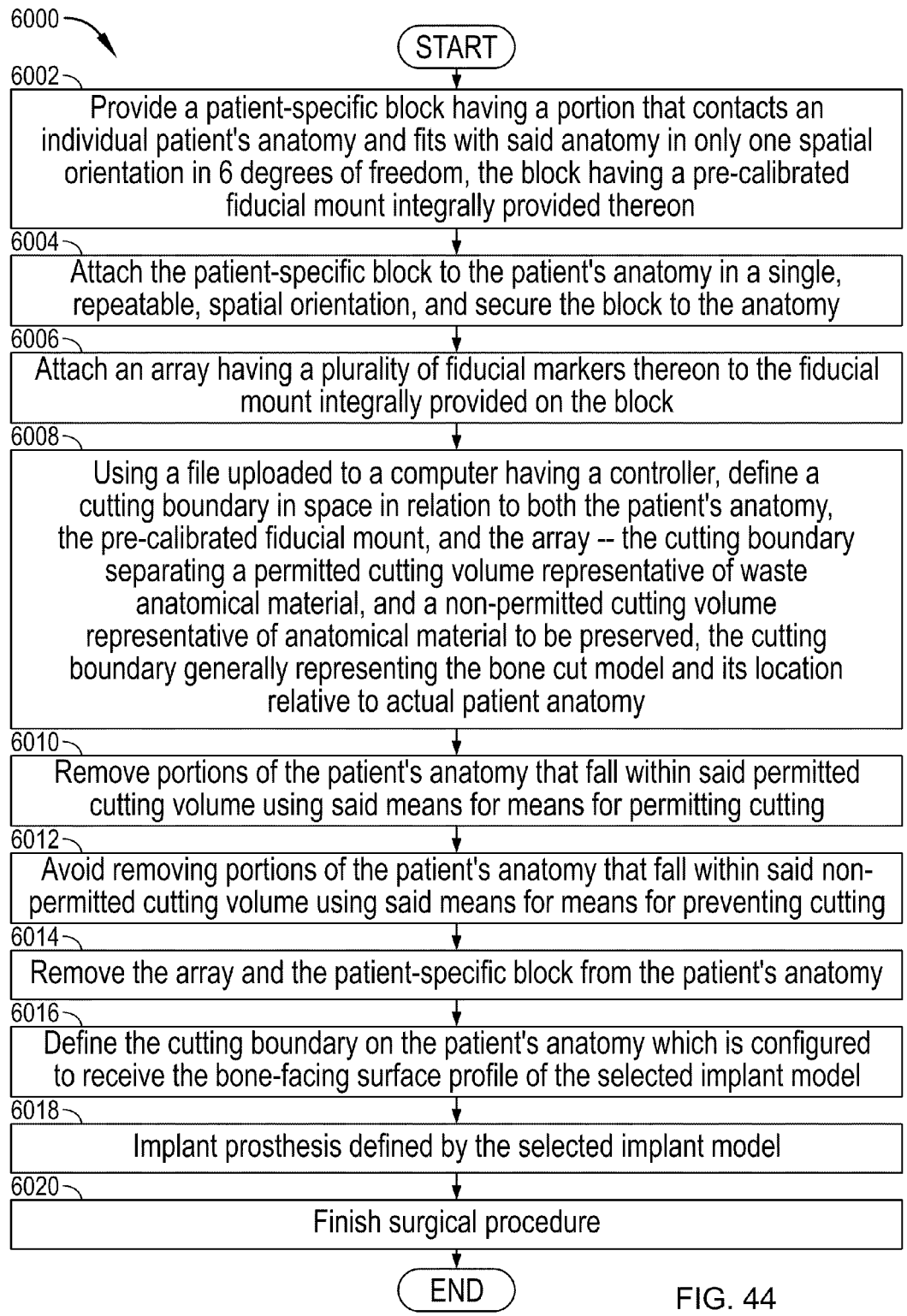
FIG. 44 schematically illustrates a method according to some embodiments.

FIG. 44 describes an alternative system and method wherein mount 2400' may be integrally provided with an anatomy-facing portion configured to conform to and mate with a patient's anatomy 9000' in one spatial orientation within six degrees-of-freedom. The anatomy-facing portion can conform to and mate with the patient's anatomy 9000' via a surface contact, a line contact, or a point contact, such that a separate patient-matched block 2000 as shown and described in FIGS. 23-31 is not necessary. The mount 2400' is placed onto the patient's anatomy 9000' in only one spatial orientation, and then is secured to the anatomy 9000' with surgical fasteners 2203', 2205' as shown in FIGS. 28-39. The procedure is finished in a similar manner as described for FIG. 43.

Those with ordinary skill in the art will recognize that the markers, calibration methods, and tracking methods provided herein are merely illustrative, and other methods of finding coordinates on the workpiece and/or cutting tool surface can be used, including for example, ultrasound, fluoroscopic imaging, electromagnetic sensors, optical range sensors, mechanical arms, etc.

The tracking system can be, for example, as described in U.S. Pat. Nos. 5,828,770; 5,923,417; 6,061,644; and 6,288,785, the contents of which are incorporated herein by reference. Other tracking systems may be employed, such as radio-frequency (RF) tracking, ultrasound tracking, electromagnetic tracking, including "Flock of Birds" tracking, as those described in U.S. Pat. Nos. 4,849,692; 5,600,330; 5,742,394; 5,744,953; 5,767,669; and 6,188,355, the contents of which are incorporated herein by reference.

Figure 45:
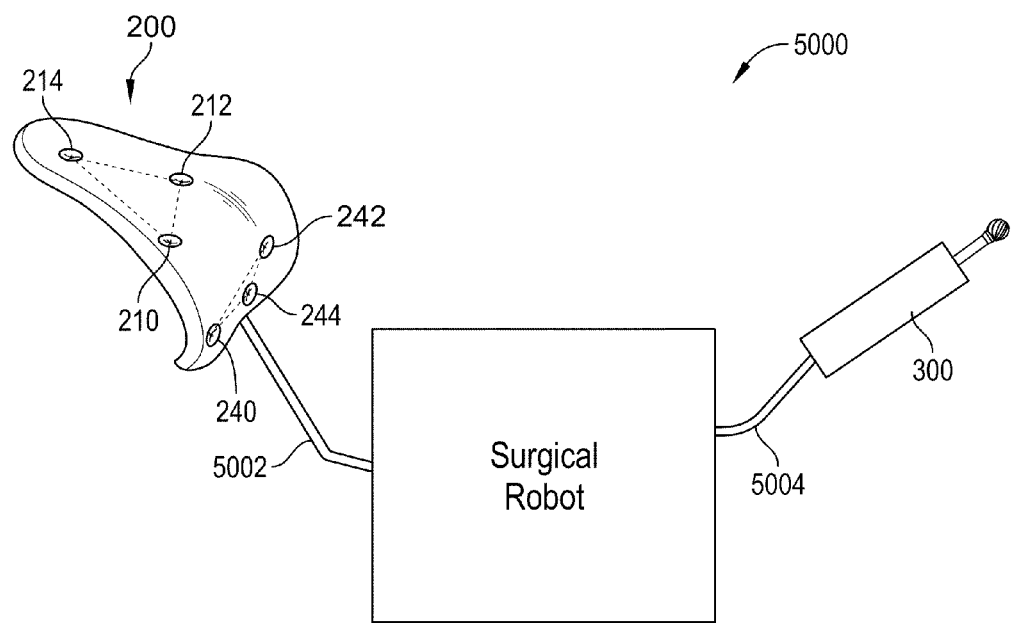
FIG. 45 shows a surgical robot according to some embodiments.

The systems and methods described herein may also be used in an automated robotic surgery. FIG. 45 shows a surgical robot 5000 having a first arm 5002 for fitting the patient-matched instrumentation block 200 or 2000 to the patient's bone and a second arm 5004 configured to receive a cutting tool (e.g., surgical tool 300 as shown in FIG. 11)

for resecting the patient's bone according to a surgical plan. A technician may fit the block 200 to the first arm 5002, the first arm 5002 being guided by the surgical robot 5000 to correctly align the block 200 with respect to the patient's bone. Once the block 200 is fitted to the patient's bone, the robot 5000 may register the location of the patient's bone by joining a registration tool (e.g., tool 300) operated by the second arm 5004 to one or more of the registration portions 210, 212, 214, 240, 242, and 244 located on the block 200. Alternatively, a technician or surgeon could places the block 200 directly on to the patient's bone and the surgical robot 5000 could register and resect the patient's bone according to a predefined surgical protocol and a cutting boundary. One example of the surgical robot 5000 may be the PiGalileo surgical navigation system sold by Smith & Nephew, Inc.

Various implementations and embodiments of the systems and methods disclosed herein (and any devices and apparatuses), and any combinations thereof, will be evident upon review of this disclosure. For example, certain embodiments include a patient-matched apparatus (for example a patient-matched block 200) for registering the location of a surgical tool. The apparatus includes an inner surface that conforms to an image of the patient's anatomic portion (such as a bone) and a body having one or more registration sites configured to receive a registration tool. The registration site may include one or more registration points corresponding to one or more reference markers described in the image of the patient's anatomic portion. The image may be disclosed, described or displayed as a computer image or any other graphical, electronic or other image.

The inner surface of any of the apparatuses may be configured to fit the patient's anatomic portion in a pre-determined spatial orientation, for example fitting the anatomic portion in only one spatial orientation. The registration site of any of the aforementioned patient-matched apparatuses may include a partially spherical surface.

Any of the registration tools disclosed herein or used in connection with any of the aforementioned patient-matched apparatuses or systems or methods may include a cutting member that interfaces with the registration site to identify a location of the registration site and communicates that location to a computer. The registration tool may communicate the location of the registration point relative to a reference array for storing into the computer in a first file. In various embodiments, the computer may include one or more of tracking hardware, tracking software, and a controller for guiding the surgical tool according to a second file containing a surgical plan. In the foregoing embodiments, the cutting member of the surgical tool may include a center that corresponds to the registration point of the patient-matched block or apparatus. The registration point of any of the patient-matched apparatuses may correspond to a reference marker. Any of the registration points may correspond to a reference marker of an iterative biomechanical simulation model of the patient.

In various implementations, a method is provided for operating a surgical alignment guide. The method includes the step of providing at least one registration site on a patient-matched apparatus. The apparatus may have an inner surface that conforms to a contour of an image of a patient's anatomic portion. The method may also include one or more of the steps of: providing a surgical tool with an alignment point configured to interface with the registration site; and align the alignment point with respect to the registration site for communicating the location of that registration site to a processor; tracking the position of the surgical tool relative to a reference array to identify the position of the surgical tool; defining a physical boundary for the surgical tool; guiding the operation of the surgical tool depending on the location of the surgical tool with respect to the physical boundary of the surgical tool; displaying a relative position of the surgical tool with respect to the physical boundary on a display device; communicating the position of the registration site to a processor via a tracking receiver; or any combination thereof.

In various implementations, a method is provided for manufacturing a surgical alignment guide. The method comprises one or more of the steps of: creating a computer model of a patient's joint based on an image of the patient's joint; creating at least one reference point on the computer model of the patient's joint; defining a spatial relationship between the reference point and a bone surface of the computer model of the patient's joint; creating a patient-matched alignment guide having at least one site that correspond to the reference point; creating an inner surface of the patient-matched alignment guide, the inner surface having a profile that conforms to a contour of the image of the patient's joint; or any combination thereof.

In various implementations, a system is provided for registering a location of a patient's anatomic portion using a patient-matched apparatus (such as a block). The system includes a patient-matched apparatus having a first connector and an anatomy-facing surface that conforms to an image of the patient's bone; and a mount having a second connector that mates with the first connector and is configured to receive an array to communicate a location of the array to a computer assisted surgical system. The mount may be positioned in a fixed spatial relationship with respect to the anatomy-facing surface. The systems may include a surgical tool having a second array configured to communicate a location of the surgical tool with respect to the first array.

In various implementations, a system is provided for operating a surgical alignment guide. The system includes a patient-matched surgical apparatus having an inner surface that conforms to an image of a patient's bone and an alignment site; a registration tool configured to interface with the alignment site to relate the position of the patient-matched surgical apparatus to a surgical tool; and a processor that tracks a location of the surgical tool with respect to an array.

In various implementations, a patient-matched surgical guide is disclosed for registering a location of a patient's bone. The surgical guide may include an inner surface that conforms to the patient's bone; and a body having a registration site that receives a registration tool of a medical device for communicating the location of that registration tool to a processor, wherein the registration site includes a registration point that corresponds to a reference marker described in an image of the patient's bone. The inner surface of the inner surface may be configured to fit a portion of the patient's bone in only one spatial orientation. In any embodiment of such guide, the registration site of the patient-matched surgical guide may include a partially spherical surface. In any embodiment of such guide, the image may be a three-dimensional model of the patient's bone, and the marker may define a spatial relationship with respect to the articulating surfaces of the patient's bone. In any embodiment of such guide, the image may be of a virtual surgery model.

In various implementations, a system is provided for registering a location of a patient's anatomic portion using a patient-matched block. The system includes a patient-matched block having an anatomy-facing surface that conforms to a patient's bone and a connector; and a mount that attaches to the bone and the connector and is configured to receive an array to communicate a location of the bone to a computer assisted surgical system. In any embodiment of such system, the mount may be positioned in a fixed spatial relationship with respect to the anatomy-facing surface.

In various implementations, a system is provided for performing a computer-assisted surgical procedure for implanting a prosthetic device to a patient. The system includes a patient-matched block having a registration site and an inner surface that is configured to conform to a patient's bone; a surgical tool with a cutting tip that interfaces with the registration site to identify a location of the registration site; and a processor that tracks the location of the tool with respect to the location of the patient's bone. In any embodiments of such system, a computer may be included and may have one or more of tracking hardware; tracking software; and a controller for guiding the surgical tool according to a file containing a surgical plan. In any embodiments of such system, the registration site of the patient-matched block may include a partially spherical surface having a center registration point. In any embodiments of such system, the cutting tip may include a center that corresponds to the registration point of the patient-matched block. In any embodiments of such system, the registration site may include a registration point that corresponds to a reference marker of a three-dimensional model of the patient's bone. The registration point may correspond to a reference marker of a completed virtual surgery model. In any embodiments of such system, a first file may be included and contain data of the location of the registration site of the patient-matched block relative to the patient's bone. In any embodiments of such system, a tracking receiver is in communication with the processor, the tracking receiver being configured to identify the location of the registration site.

In various implementations, a method of operating a surgical alignment guide is provided. The method includes one or more of the steps of: providing a patient-matched block, the block having at least one registration site and an inner surface that conforms to an anatomic portion of the patient; providing a surgical tool with an alignment point that interfaces with the registration site; aligning the alignment point with respect to the at least one registration site; tracking the position of the surgical tool relative to a reference array to identify the position of the tool; defining a cutting boundary having one or more pre-planned optimized resections of the patient's anatomy; or any combination thereof.

In various implementations, a system is provided for performing a computer-assisted surgical procedure for implanting a prosthetic device to a patient, the system comprising a patient-matched surgical apparatus having an inner surface that conforms to the patient's bone and an alignment site; a registration tool configured to interface with the alignment site to identify the location of the patient's bone; and a processor that tracks a location of a surgical tool with respect to an array.

In view of the foregoing, it will be seen that the several advantages are achieved and attained. As various modifications could be made in the constructions and methods herein described and illustrated without departing from the scope, it is intended that all matter contained in the foregoing description or shown in the accompanying drawings shall be interpreted as illustrative rather than limiting.

Variations and modifications will occur to those of skill in the art after reviewing this disclosure. The disclosed features may be implemented, in any combination and subcombinations (including multiple dependent combinations and subcombinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made part of this application.

What is claimed is:

1. A patient-matched surgical guide for registering a location of a patient's bone, the surgical guide comprising:
   an inner surface that conforms to the patient's bone; and
   a registration site formed in a non-bone contacting surface that receives a registration tool of a medical device for communicating the location of that registration tool to a processor,
   wherein the registration site includes a registration point that corresponds to a reference marker described in an image of the patient's bone, and
   wherein the registration site does not extend to the inner surface.

2. The surgical guide of claim 1, wherein the inner surface is configured to fit a portion of the patient's bone in only one spatial orientation.

3. The surgical guide of claim 1, wherein the registration site of the patient-matched surgical guide includes a partially spherical surface.

4. The surgical guide of claim 1, wherein the image is a three-dimensional model of the patient's bone, the marker defining a spatial relationship with respect to the articulating surfaces of the patient's bone.

5. The surgical guide of claim 1, wherein the image is of a virtual surgery model.

6. The surgical guide of claim 1, wherein the registration site comprises a recess.

7. The surgical guide of claim 6, wherein the non-bone contacting surface is located opposite the inner surface.

8. The surgical guide of claim 6, wherein the registration site is shaped to mate with a complementary shape of a tip of the registration tool.

9. The surgical guide of claim 8, wherein the registration point aligns with a center of the tip when the registration tool is placed within the registration site.

10. The surgical guide of claim 1, wherein a first registration distance is defined between the registration point and a surface of the patient's bone.

11. The surgical guide of claim 10, wherein the first registration distance is a thickness of the guide.

12. The surgical guide of claim 10, wherein a second registration distance is defined between the registration point and a planned resection surface.

13. The surgical guide of claim 12, wherein the difference between the second registration distance and the first registration distance corresponds to a depth of material to be removed.

14. The surgical guide of claim 1, further comprising at least three registration sites, each having a respective registration point, wherein the respective registration points together define a reference plane.

15. The surgical guide of claim 1, wherein the registration tool electronically communicates the location of the registration tool to the processor.

16. The surgical guide of claim 15, wherein the location of the registration tool is electronically communicated to the processor when the registration tool engages the registration site.

* * * * *